US007244225B2

(12) United States Patent
Loeb et al.

(10) Patent No.: US 7,244,225 B2
(45) Date of Patent: Jul. 17, 2007

(54) DEVICES AND METHODS FOR NON-INVASIVELY IMPROVING BLOOD CIRCULATION

(75) Inventors: Marvin P. Loeb, Huntington Beach, CA (US); Ginger Johnson, Newport Beach, CA (US); John P. Burrell, Tustin, CA (US); Robert J. Sullivan, Lake Forest, CA (US); Lawrence J. Perkins, Anaheim, CA (US)

(73) Assignee: Cardiomedics, Inc., Irvine, CA (US)

( * ) Notice: Subject to any disclaimer, the term of this patent is extended or adjusted under 35 U.S.C. 154(b) by 383 days.

(21) Appl. No.: 10/681,812

(22) Filed: Oct. 7, 2003

(65) Prior Publication Data

US 2005/0075531 A1 Apr. 7, 2005

(51) Int. Cl.
*A61N 1/362* (2006.01)

(52) U.S. Cl. ........................................................ 600/17

(58) Field of Classification Search .................. 600/16, 600/17; 601/149, 152; 606/201, 202, 204
See application file for complete search history.

(56) References Cited

U.S. PATENT DOCUMENTS 3,288,132 A 11/1966 Meredith .................... 601/152
3,303,841 A 2/1967 Dennis ........................ 601/152
3,403,673 A 10/1968 MacLeod ........................ 601/9
3,654,919 A 4/1972 Birtwell ........................ 601/152
3,734,087 A 5/1973 Sauer et al. ................ 601/152
3,835,845 A 9/1974 Maher ........................ 601/150
3,866,604 A 2/1975 Curless et al. .............. 601/152
4,388,919 A 6/1983 Benjamin, Jr. et al. ..... 601/150
4,753,226 A * 6/1988 Zheng et al. ............... 601/150
4,865,020 A * 9/1989 Bullard ........................ 601/152
5,806,512 A * 9/1998 Abramov et al. ...... 128/204.18
6,450,981 B1 * 9/2002 Shabty et al. ............... 601/150
2002/0107461 A1 * 8/2002 Hui ............................ 601/149

* cited by examiner

*Primary Examiner*—Carl Layno
*Assistant Examiner*—Eric D. Bertram
(74) *Attorney, Agent, or Firm*—Gene Scott; Patent Law & Venture Group

(57) ABSTRACT

Circulatory assistance is provided in a non-invasive procedure safely and effectively using a microprocessor of an external counter pulsation device programmed to control the actuation of any or all of a plurality of valves, each of which is mounted on and in fluid communication with one of a plurality of individual inflatable bladders disposed in pockets within cuffs encasing the calves, thighs, buttocks, abdomen and/or chest of a person and an optional valve in fluid communication with the person's airway, in any desired sequence or order, toward the heart or toward the feet, either during diastole or systole, at desired inception times during the cardiac cycle, for selected durations and at chosen pressures, for treating a variety of cardiac, non-cardiac and circulatory conditions.

32 Claims, 19 Drawing Sheets

Case 312

DEVICES AND METHODS FOR NON-INVASIVELY IMPROVING BLOOD CIRCULATION

RELATED APPLICATIONS

This application is related to a co-owned, now abandoned, U.S. patent application having Ser. No. 10/263,954 and file date of Oct. 2, 2002, which is incorporated herein by reference.

INCORPORATION BY REFERENCE

Applicant(s) hereby incorporate herein by reference, any and all U.S. patents, U.S. patent applications, and other documents and printed matter cited or referred to in this application.

BACKGROUND OF THE INVENTION

1. Field of the Invention

The present invention relates to devices and methods for non-invasively enabling blood circulation to be improved in a more effective manner than existing non-invasive circulatory assistance devices and those which require surgical intervention.

2. Description of Related Art

Current circulatory assistance procedures consist of surgically creating an opening in an artery feeding an organ or a portion of the body and a vein exiting the organ or portion of the body, inserting cannulas, catheters or large needles into the artery and vein, pumping blood at an accelerated rate from the artery through the organ or body portion and returning it to the vein. The blood may be oxygenated or otherwise treated while being circulated extra-corporeally. Such procedures require strict sterility and anti-coagulants, cause damage (hemolysis) to red cells and other blood components and entail the cost and risk of adverse events of surgery.

Some years ago, external counter pulsation or ECP devices were introduced which non-invasively provide circulatory assistance by moving blood from the extremities (legs and buttocks) up to the heart to treat angina pectoris, acute myocardial infarctions (heart attacks) and cardiogenic shock. Early ECP devices employed a liquid, typically water, to compress the extremities. Later ECP devices employed air to compress the extremities, which avoided the need to heat the water to body temperature and the risk of an electrical shock if a balloon or bladder containing the water were to leak or burst. Such early ECP devices are disclosed in U.S. Pat. Nos. 3,288,132; 3,303,841; 3,403,673; 3,734,087 and 3,835,845; as well as co-owned U.S. Pat. Nos. 3,654,919; 3,866,604 and 4,388,919, which, as stated above, are incorporated herein by reference.

Current ECP devices typically include bladders disposed in pockets within each of two pairs of cuffs, which are fastened about the calves and thighs of a person, and two bladders contained in a single cuff which is fastened about his or her buttocks. The bladders are sequentially inflated with air. First, the bladders in the cuffs about the calves are inflated. About 30 to 50 milliseconds later, the bladders in the cuffs about the thighs are inflated, followed, after about 30 to 50 milliseconds, by inflation of the bladders in the cuff about the buttocks inflation and deflation of the bladders is initiated and terminated, respectively, during diastole, after the heart has finished its compression cycle (systole) and is temporarily at rest between compressions (heartbeats). Inflation to a desired pressure is begun after a selected time delay period from the "r" wave of the person's electrocardiogram (ECG), forcing blood up the arteries (and veins) to the heart, counter to the usual direction of arterial blood flow. Compression of the cuffs continues for a selected time period, with simultaneous deflation of all of the bladders occurring during diastole, before the onset of systole, so as not to create resistance to the pumping of blood out of the left ventricle of the heart. When the bladders deflate, the air is released into the atmosphere. Alternatively, the air may be withdrawn by the application of a vacuum to the bladders.

Inflation of the bladders tightens the cuffs and forces blood from the legs and buttocks up the veins into the right heart chambers (auricle and ventricle). This reduces the work-effort of the heart, since a major portion of the heart's work is devoted to returning blood to the heart from the extremities. Inflation of the bladders also forces blood from the legs and buttocks up the arteries into the aorta. Since the aortic valve, if competent, is closed during diastole, the blood cannot enter the left heart chambers and flows from the aorta into the coronary, carotid and other arteries. An increase in intra-coronary artery pressure of up to 40% was measured during ECP, using tiny pressure transducers positioned in the coronary arteries of humans. Such transducers are manufactured, for instance, by Millar Instruments, Inc. of Houston, Tex.

A number of papers have been published on clinical studies in which ECP devices, made by the owner of the present disclosure, have been shown to be safe and effective in the treatment of Stable (chronic) Angina, Acute Myocardial Infarctions (heart attacks) and Cardiogenic Shock (the most serious complication of a heart attack), and such ECP devices have been cleared for sale by the FDA for the treatment of these conditions, as well as Congestive Heart Failure.

In the treatment of heart attacks, ECP was administered for four hours to force blood around the blockage in one or more of the coronary arteries, relieving the ischemia (oxygen deprivation) caused by the absence of blood flow and reducing the damage to the area of the heart supplied by the blocked artery or arteries. An estimated one million heart attacks occur each year in the United States with a mortality of about 50%.

The repetitive application of ECP, which has been shown to significantly increase intracoronary artery pressure, is thought to cause the release of endogenous (naturally occurring) angiogenic growth factors, resulting in the creation of capillaries and arterioles (angiogenesis) and to restore the elasticity and vitality of the endothelial lining of the arteries of the heart, which usually decline with age. To treat a chronic condition, such as stable angina pectoris (Angina) or Congestive Heart Failure (CHF), ECP is typically administered for a period of one hour, five days a week for seven weeks. It is thought that most or all of the angiogeriic agents stored in the arteries is released within one hour by ECP, and delaying the treatment for a period of time gives the body time to manufacture and restock the depots in the arteries with such growth factors. An estimated 6 million people in the United States suffer from Stable (chronic) Angina, and approximately 2.5 million suffer from CHF.

One present type of ECP device, manufactured by the owner of this application, Cardiomedics, Inc. of Irvine, Calif., consists of a control console, containing a microprocessor, associated electronics and a touch-screen display, a power supply, one or more air compressors, an air reservoir and electrically actuated solenoid valves ("Solenoid Valves"), as known in the art, which are in fluid communication with and, when actuated, release air from the reservoir. Hoses attached to and in fluid communication with the outlets of the Solenoid Valves extend about four to six feet from the Solenoid Valves to bladders disposed in pockets within cuffs, which are fastened about the patient's calves, thighs and buttocks. Such ECP devices weigh about 400 pounds, are portable and can be moved from bed to bed to treat patients, without having to move the patients from their beds.

Other present ECP devices utilize sets of cuffs and bladders about the calves, thighs and buttocks, as described above, but the air reservoir and attached Solenoid Valves are mounted beneath a bed dedicated to the treatment of patients brought to the ECP device. Such other ECP devices are described in U.S. Pat. Nos. 4,753,226; 5,554,103 and 5,997, 540. The air compressor and Solenoid Valves associated with such ECP devices may likewise be mounted beneath the bed, or may be housed in a separate enclosure. Locating the air reservoir and attached Solenoid Valves beneath the bed shortens the length of the air hoses to the bladders disposed within the cuffs to about 2 to 3 feet, slightly reducing the inflation time of the bladders and the amount of air lost from the hoses when the cuffs are deflated. However, the weight of such ECP devices is 700 to 1100 pounds, and the lack of portability generally limits their use to ambulatory patients or requires a critically ill patient to be moved on a gurney to the ECP device, moved onto the bed of the ECP device for the ECP treatment, and finally, moved back into his/her bed.

It would be desirable to further reduce the loss of air from the hoses when the bladders are deflated, as well as to not require that patients, particularly critically ill patients, be brought to the ECP device.

In our co-pending application Ser. No. 10/263,954, an advanced ECP device is described, in which lightweight, air pressure actuated valves ("APA Valves") are attached directly to the individual inlets of bladders disposed within pockets in the cuffs, which are fastened about the calves, thighs and buttocks of the patient. An operating air pressure is maintained in a pneumatic trunk line that extends from a low pressure air reservoir (maintained at up to 10 psi, preferably about 6 psi) and branches into smaller branch pneumatic lines connected to the APA Valves attached to the individual inlets of each of the bladders within the cuffs. The APA Valves, when actuated, admit air into the bladders or allow air to escape through an exhaust port. The APA valves may be spool valves or any other type of valve known in the art.

Air pilot lines are attached to, in fluid communication with, and extend from each of the Solenoid Valves, which are in fluid communication with a high pressure air reservoir (pressurized from about 12 to 30 psi, preferably about 15 to 26 psi). The air pilot lines extend to the APA Valves attached to the inlets of the bladders disposed in the cuffs. By positioning the APA Valves at the inlets of each bladder, pressure is maintained at all times in the trunk and branch pneumatic supply lines. This minimizes the time of inflation of the bladders and significantly reduces the amount of air lost during the exhaust cycle when the bladders are deflated, reducing the size and weight of the compressor(s), reservoir, and power supply of the ECP device. Actuating the APA Valves attached directly to the bladders of the cuffs with air pressure through the air pilot lines, instead of electrically, eliminates the risk of an electrical shock to the patient.

The presence of buttock cuffs in the current ECP devices described above, however, makes it difficult or impossible to insert a catheter into the femoral artery in the patient's groin area, which is required in persons undergoing an angiogram, coronary balloon angioplasty, insertion of an intra-aortic balloon or other cardiac catheterization procedure which may be required in the treatment of the patient. Furthermore, the current ECP devices described above inflate their three sets of cuffs in a fixed sequence, first the calves, then the thighs and finally the buttocks, limiting their use to treating conditions in which such three cuff sequence is desirable. Also, both of the above described ECP devices are programmed to permit compression of the cuffs only during diastole, and the current ECP devices compress the cuffs about both legs of a patient and do not provide for individual cuff inflation, which would be beneficial in the treatment, for example, of an amputee or a person with a broken leg.

As a result, it would be desirable to have an ECP device not subject to the above limitations.

In the treatment of Angina, heart attacks or cardiogenic shock, the patient may suffer from premature ventricular contractions or "PVC's", which can produce a wide "qrs" interval in the ECG pattern (the time from the end of the "q" wave to the start of the "s" wave), which the microprocessor recognizes and ceases actuation of the Solenoid Valves. Persons with a very low heart rate or an HIS bundle branch block, which is typically treated by implanting a cardiac pacemaker, often produce wide "qrs" intervals in the patient's ECG patterns that are recognized as PVC's by the microprocessor, which causes immediate cessation of actuation of the inflation valves.

It would be desirable to be able to overcome these limitations and provide for a means to enable the operator to over-ride the customary computer program of present ECP devices o treat such patients.

In the treatment of cardiac arrest outside a hospital, cardiopulmonary resuscitation or "CPR" is often applied. The chest is manually compressed by a bystander, who periodically pinches the patient's nose to close the nasal air passages and breathes into the patient's mouth to fill the lungs with air. However, survival from cardiac arrest outside a hospital is very low. This is because manual CPR does not effectively return the blood, which is forced out of the heart by compressing the chest, back to the heart. Also, air breathed into the patient's mouth contains significantly less oxygen and more carbon dioxide than ambient air. Mechanical chest compression devices suffer from the same lack of return of blood to the heart.

When paramedics arrive, a mechanical ventilator, such as the Ambu® MediBag® manufactured by Ambu, Inc. of Linthicum, Md., may be used. The bag is manually squeezed to force ambient, air into the lungs. The paramedics may also apply an electrical shock to the chest to defibrillate and restore the heart to a normal rhythm. However, the weakened heart must continue to work hard to pump blood to the feet and back, and a subsequent cardiac arrest may occur, which may prove fatal.

It would be desirable to have a non-invasive, circulatory assist device that could improve circulation and assist the heart of a person in cardiac arrest, and which could also be used for hours after the patient is resuscitated to reduce the heart's work effort and, perhaps, prevent a subsequent cardiac arrest. The present invention teaches certain benefits in construction and use, which give rise to the objectives described above.

In the treatment of CHF, the patient frequently has a left ventricle ejection fraction less than 40% (55% is normal), due to the inability of the heart to efficiently pump and eject the blood from the main pumping ventricle of the heart. Since ECP increases the flow of blood into the ventricles, excessive pre-loading of the heart can occur in these patients, which could worsen their condition or be fatal. It would be desirable to have an ECP device and a method of use that would prevent this event from occurring.

The present invention fulfills these needs and provides further related advantages as described in the following summary.

SUMMARY OF THE INVENTION

The present invention teaches certain benefits in construction and use, which give rise to the objectives described below.

The present invention consists of an improved ECP device whose microprocessor, upon commands transmitted from a display screen, such as a touch-screen display, is programmed to actuate or not actuate any of the valves which inflate the bladders of any of the cuffs, at a time separate from the actuation of the valves which inflate the bladders in the other cuffs, in any desired sequence, forcing blood either toward the feet or toward the heart, during either diastole or systole. The present invention also enables an ECP device to more safely and effectively treat persons with a cardiac pacemaker, who suffer from CHF, who are in cardiac arrest or suffer from certain other conditions, as described below.

Good health is dependent on the vitality and functionality of all of the body's systems: circulatory, nervous, musculoskeletal, pulmonary, digestive, urinary, endocrine and others. If blood flow is inadequate to support the function of any of the body's main systems, poor health and death can result.

The present invention, properly applied, is able to therapeutically treat cardiovascular related conditions such as: acute myocardial infarctions, chronic and acute CHF, pre and post ptca, pre and post CAGB surgery, unstable angina, ischemic stroke, cardiac arrest, atrial fibrillation, ventricular fibrillation, ventricular tachycardia, mitral valve prolapse, hypertension, aortic incompetence or regurgitation, peripheral artery disease, gangrene, peripheral edema, pulmonary edema, retinal ischemia and erectile dysfunction; and cardiopulmonary related conditions such as: chronic obstructive pulmonary disease and emphysema; endocrine related conditions such as diabetes; clearance (shear force related conditions such as acute renal kidney failure, septic shock, end stage renal disease, acute hepatic (liver) failure and chronic obstructive pulmonary disease; and brain and nervous system related conditions such as sleep apnea, epilepsy, anxiety disorders, depression, diabetic neuropathy, chronic migraine headaches, insomnia, senile dementia, cognitive deficits, Alzheimer's disease and Parkinson's disease and to prevent deep vein thrombosis, as well as similar and related illnesses, conditions and dysfunctions; all of which shall be referred to as "medical conditions" in this specification and the claims.

Reversing the sequence of inflation of the bladders in the cuffs (first compressing the buttocks, next the thighs' and then the calves) forces blood toward the feet. Such reverse sequence ECP may be employed during diastole, for example, to treat edema in the legs, ankle and/or feet, a condition frequently occurring in patients with congestive heart failure, peripheral vascular disease and other conditions.

Multiple organ failure (often referred to as septic shock) affects about 200,000 people each year in the United States and presently has a 50% mortality rate. To improve perfusion of the kidneys, liver, pancreas and other internal organs in the treatment of septic shock, it would be desirable to apply ECP during systole. The hearts of most septic shock patients are often strong enough to withstand the effect of enhanced blood flow into the heart during systole, when the aortic valve is open, against the heart's compression, as septic shock patients often have normal or elevated cardiac output. Warren R. Summers, M. D., employed ECP during systole in four multiple organ failure (septic shock) patients at Louisiana State University Medical Center in New Orleans, using an ECP device programmed to compress the cuffs during systole, which was specially modified by the owner hereof. Each of the patients, who had a Swan Ganz and arterial catheter in place for hemodynamic monitoring, received 15 to 30 minutes of ECP therapy each day for six days. ECP increased their mean arterial pressure, cardiac output, oxygen delivery, regional distribution of blood flow and renal organ (kidney) perfusion.

Many persons suffering a heart attack or other cardiac event must have a catheter inserted into their femoral artery in the groin, for example, to monitor their cardiac functions or to inject a radio-opaque liquid to ascertain by X-ray imaging the location and degree of blockage in a coronary artery. To enable the use of such a catheter, de-activating the valves that inflate the bladders of the buttocks cuff allows the buttocks cuff to not be used. ECP may then be provided, as described above (first the calves, then the thighs) during diastole, to treat a catheterized patient suffering from unstable angina, an acute myocardial infarction or cardiogenic shock. If desired, after the catheter has been inserted, or after the procedure has been completed, the buttocks cuff can be attached to the patient and the valves actuated to inflate the bladders contained therein.

Applying ECP during diastole as described above, without using the buttocks cuff (compressing first the calves, then the thighs), may also be beneficial in performing coronary artery balloon angioplasty, which requires frequent femoral artery access to insert and remove guide wires and balloon catheters. The application of calf/thigh ECP during balloon angioplasty may increase coronary artery blood flow and eliminate the chest pain experienced by many patients during the balloon's inflation, which blocks blood flow in the affected coronary artery and causes ischemia (oxygen deprivation) of the portion of the heart muscle supplied by such artery. The use of such an ECP device may also allow for slower, gentler inflation of the balloon and a longer inflation period, for example, up to about 5 minutes or longer, from the present balloon inflation time limit of about one minute. Slow inflation of the angioplasty balloon may eliminate "cracking the plaque" and reduce damage to the artery wall. Also, the substantially longer inflation time may allow a dissected section of plaque to be held in place long enough for it to reattach itself and reduce the incidence of abrupt or later closure of the vessel.

To treat gangrene in the calf, ankle and/or foot, inflating the bladders in the buttocks cuff and the thigh cuffs may be employed, during diastole or systole, without inflating the bladders of the calf cuffs, which could be painful to the patient. To treat impotency, which may be due to plaque blockage of the pudental artery or some other circulatory-related cause, only the inflation valves inflating the bladders of the calf and thigh cuffs may be actuated; in that order, during diastole, eliminating the use of the buttocks cuff.

In the improved ECP System described above, where individual air pressure actuated valves ("APA Valves") are mounted directly on the inlets of each of the individual bladders in the cuffs, any or all of the air pilot line Solenoid Valves, which allow air to enter the air pilot lines and actuate the APA Valves, may or may not be actuated. Furthermore, the Solenoid Valves, which admit, when actuated, air into the air pilot lines, can be actuated in any desired sequence, forcing blood either toward the heart or toward the feet, during either diastole or systole.

For example, in the case of an amputee, a patient who recently underwent surgery in one leg (such as removal of the sapphenous vein for use in bypass surgery) or who suffered a broken leg, who is also suffering from a medical condition treatable with ECP, only the bladders of the cuffs about the remaining or undamaged leg may be inflated. In treating a medical condition in a patient, for example, who recently underwent kidney, prostate or other abdominal surgery, or one who suffered a broken hip, the inflation valves of the buttocks cuff may not be actuated, while any or all of the inflation valves of the bladders in the calf and/or thigh cuffs may be actuated in any desired sequence, during systole or diastole, as described above.

The microprocessor of the improved embodiment of the present invention can also be programmed to adjust, upon selection by the operator, the amount of air pressure applied to any or all of the bladders of the cuffs. For example, less pressure may be applied to the bladders in the cuffs of one leg of a person with a wound, who suffered a broken bone or had a vein removed from that leg, to avoid causing pain.

An air relief or check valve can be attached to the exhaust port of the APA Valves and manually set or microprocessor controlled to release into the atmosphere all but a selected residual amount of air pressure in the bladders after their deflation. This further reduces the volume of air lost when the bladders deflate and the size, power requirement and weight of the compressors of the ECP device. The residual pressure, for example, about 0.3 to 0.7 psi, preferably about 0.4 to 0.6 psi, may take up any unused space between the cuff and the portion of the body it encloses, without creating resistance against blood flow out of the heart on its next compression.

The survival rate after a cardiac arrest is very low, especially if it occurs outside of a hospital setting. A bystander may apply cardiopulmonary resuscitation or "CPR" by manually compressing the chest and, periodically, breathing into the patient's mouth, or a paramedic may use a mechanical ventilator and apply a shock to produce a normal heart rhythm. However, there are no means to return the blood, which has been squeezed out of the heart by compressing the chest, back to the heart. Even if CPR restarts the heart or an electrical shock is applied to the chest, the restarted heart may fail again due to the work effort of pumping blood to the feet and back to the heart. While a number of automated chest compression devices have been tried, none has proved successful in increasing survival from cardiac arrest, as again, there is no means to return the blood from the extremities to the heart. Also, air breathed into the patient's mouth from the person performing the CPR procedure contains a significant amount of carbon dioxide and less oxygen than ambient air.

A preferred embodiment of the present invention entails the use of an ECP device whose microprocessor has been programmed to perform ECP without an acceptable ECG signal from the patient, inflating the bladders and compressing the calves, thighs and buttocks (in that order) a selected number of times per minute at selected pressures and periods of time. The paramedic or nurse administering CPR can synchronize his or her manual compressions of the chest with the ECP device's compressions, instead of mentally counting "one thousand, two thousand," etc.

A most preferred embodiment of the present invention entails the use of an additional cuff, which is fastened with Velcro® about the patient's chest. Two or more bladders are disposed within pockets in the chest cuff. Individual, APA Valves are attached to the inlets of each of the bladders in the chest cuff, and individual air pilot lines, each leading from at least one, Solenoid Valve in fluid communication with the high pressure air reservoir of the ECP device, are attached to, in fluid communication with, and actuate the aforesaid APA Valves, to each of which a pressurized branch air hose is removeably attached, as described heretofore. While one chest cuff is described above, two or more chest cuffs or a chest cuff and an abdominal cuff may be utilized.

A further modification of the most preferred embodiment described above may include the microprocessor actuating an additional Solenoid Valve in fluid communication with the aforesaid high pressure air reservoir, which, through a separate air pilot line, causes an APA Valve attached to a mouthpiece to be actuated about 13 to 16 times per minute, preferably about 14 to 15 times per minute, to force air into the patient's lungs. An air pressure regulator attached to the APA Valve admits air from a separate, pressurized branch air hose through the mouthpiece into the patient's airway at a desired pressure. The air pressure regulator can be manually set or controlled by the microprocessor, based on data from an air pressure sensor within the air hose in fluid communication with the APA Valve, to deliver the amount of air pressure selected by the operator on the display screen to avoid over-inflation of the lungs. Alternatively, the APA Valve attached to the mouthpiece can be a variable output or proportional valve, whose output is controlled by the microprocessor, with feedback from a pressure sensor mounted within the air tube of the mouthpiece.

The mouthpiece can include a soft rubber or plastic lip cover to assure a good seal, an attached nose pinch to shut off the nasal passages, and a headband or strap, which can be fastened about the patient's head with Velcro® to hold the mouthpiece in the patient's mouth. Alternatively, the APA Valve can be mounted on and in fluid communication with an intubation tube inserted through the patient's mouth into his/her airway or a mask fastened over the patient's mouth and nose.

The advantage of this most preferred embodiment of the present invention is its ability to function as an automated cardiopulmonary resuscitation or "Auto-CPR" device to treat persons suffering a cardiac arrest.

The microprocessors of current ECP devices are programmed to compare the patient's ECG with an ECG pattern within normal limits. Such limits are generally a heart rate of 45 to 120 beats per minute, a recognizable and commonly sized "r" wave of the ECG and a "qrs" interval not exceeding 300 milliseconds, as well as other normal ECG indices. When an ECG pattern outside normal limits is recognized by the microprocessor, actuation of the valves, which inflate the bladders of the cuffs is immediately ceased. When the heart of a person in cardiac arrest is returned to a normal rhythm, the microprocessor can sense the restoration of an ECG signal within its programmed normal limits and, while continuing the compression of the calf, thigh and buttocks cuffs at the pre-selected parameters, cease actuation of the valves which inflate the bladders of the chest cuff and admit air into the mouthpiece or intubation tube. The inactive chest cuff and the mouthpiece or intubation tube, with the outlet open to enable the patient to breathe, may be left in place. Alternatively, the microprocessor may sound an audible alarm or send a signal to the nursing station to alert nursing personnel to remove the chest cuff and mouthpiece or intubation tube. A nurse alerted by the alarm or signal to the nursing station can also adjust the pressure, inception and duration of compression of the cuffs, based upon the patient's restored ECG pattern and blood pressure indicated by a finger or ear plethysmograph.

The ECP device can continue to compress the calves, thighs and buttocks, during diastole, of a resuscitated patient for a number of hours to reduce the work effort of the damaged heart. If the patient goes back into cardiac arrest and the microprocessor recognizes that an acceptable ECG signal has been lost, if the chest cuff and mouthpiece or intubation tube have been left in place, both can be re-activated at the earlier selected parameters. Alternatively, an audible alarm or a signal to a patient monitoring station may be sent, the chest cuff and mouthpiece may be re-applied and actuation of the APA Valves of the chest cuff and mouthpiece or intubation tube can be resumed.

The improved ECP device of the present invention enables the operator to over-ride the programmed limitations of the microprocessor to enable the allowable "qrs" interval of the ECG pattern to be increased or decreased in the treatment of patients known to have a very low or fast heart rate or a pacemaker, for example. The improved ECP device also enables the operator to over-ride the programmed intervals of 30 to 50 microseconds between compressions of the calf, thigh and buttocks cuffs, for example, to treat an obese patient or a person with a very slow or fast heart rate, such as one whose heart rate is less than 45 or greater than 120 beats per minute.

When ECP is used to treat a person suffering from severe, chronic Angina, the highest compression pressure, the longest duration of compression and the shortest delay time consistent with patient comfort are selected to produce the highest possible peak diastolic to peak systolic pressure ratio "D/S Ratio", usually between 1.5:1 and 2:1 or higher. When the calf, thigh and buttocks cuffs are compressed during diastole, forcing blood up the arteries toward the heart, diastolic pressure is increased, and blood flow from the aorta through the coronary arteries to the heart muscle increases. A high D/S Ratio increases intra-coronary artery flow and pressure and stimulates the release of angiogenic growth factors to cause angiogenesis. At the same time, compressing the extremities and buttocks forces blood up the veins into the right auricle of the heart, filling the chamber with blood, which then flows into the right ventricle. This latter effect is called "pre-loading the heart'.

CHF, which affects an estimated 4 million people in the United States, causes approximately 400,000 deaths per year, a number equal to the deaths from all types of cancer combined. Other than dual chamber, heart "resynchronization" pacemakers, which are extremely expensive (implantation of such a device in the U.S. costs $50,000 or more), require surgery and have shown only a reduction in mortality of 30% according to statistics from the American Heart Association for annual mortality from CHF in the United States, there is presently no truly effective therapy for CHF.

However, if ECP is used to treat CHF patients who typically have weak left ventricular function, excessive pre-loading of the heart can occur if the bladders of the cuffs are inflated at too high a pressure, are inflated too soon after the "r" wave of the patient's ECG or are allowed to remain compressed for too long a period of time. When there is excessive pre-loading of the heart, particularly in CHF patients with a low left ventricle ejection fraction, the heart cannot pump out or "eject" a sufficient amount of blood. This causes blood to "pool" in the blood vessels of the lungs, abdomen and extremities and fluid to build up in the lungs, calves, ankles and feet. The heart muscle works harder, causing it to thicken, which further reduces its pumping efficiency. As a result, more fluid builds up in the lungs, making it difficult for the patient to breathe, and a recurrence or worsening of heart failure or death can result.

When the compression pressures, delay times and compression durations common to the treatment of Angina are used to treat CHF patients, particularly those with low ejection fractions, many of them do well for the first 5 to 15 hours of ECP therapy, after which their CHF symptoms return and their condition is often worsened, which can lead to death. We have discovered that this problem can be avoided by limiting the D/S Ratio during the 35 hour daily, one-hour ECP treatments to between 0.7:1 to 0.8:1 during the first five hours of ECP therapy, 0.8:1 to 0.9:1 during the next five to ten hours of ECP therapy and 0.9:1 to 1.3:1 during the remainder of the 35 hour ECP regimen.

In a recent study (unpublished data) on the treatment of CHF, using an ECP system manufactured by the owner hereof, 130 persons who suffered from both New York Heart Association Class II, III or IV CHF and Canadian Cardiovascular Society Functional (CCSF) Class III or IV refractive, stable Angina, received 35 one-hour long ECP treatments using the daily regimen described above. They experienced an average increase of 20% in their ejection fractions (a recognized indicator of CHF severity), from 33% to 41.2%. In addition to significant improvement in their quality of life and other factors, in the year prior to ECP treatment, hospitalization was required an average of 1.8 times per patient, whereas in the year following ECP therapy, hospitalization was needed an average of only 0.5 times per patient, a reduction of 72%.

In the year following ECP therapy 7 deaths occurred in this group of 130 severe CHF patients, for a mortality of only 5.4%, a reduction of 71.1% from the 18.7% annual mortality rate for CHF in the United States, according to the American Heart Association's Heart Failure and Stroke 2003 Update. Using this mortality figure, 24 deaths would be expected over a one year period in a general population of 130 CHF patients receiving conventional therapy, approximately 30% of whom typically suffer from Angina. Mortality in a group of 130 severe CHF patients, all of whom also suffer from severe Angina, would be expected to be significantly higher than 18.7%.

In 54 of the chronic CHF patients in the above described 130 patient study, the D/S Ratios were limited to an average of less than 1 to 1. In these patients, mortality in the year following ECP treatment was reduced to zero, left ventricular ejection fractions increased 23% and hospitalizations were reduced to 0.4 per year, an 86% reduction. These results demonstrate the benefits of the reduced D/S Ratio regimen.

In the improved ECP device of the present invention, in the treatment of CHF, if the D/S Ratio exceeds or falls below the selected ratio, the microprocessor of the improved ECP device senses the change in the D/S Ratio and increases or decreases the compression pressure to maintain the selected D/S Ratio. In a further preferred embodiment, the delay time and duration of compression may also be adjusted by the microprocessor to maintain the selected D/S Ratio.

ECP creates a "training effect" on the heart, causing it to accommodate the repetitive inflows of both venous and arterial blood. As a result, separating the ECP treatments by more than one day may be more physiologically beneficial in the treatment of CHF patients, for example, for one hour every other day, particularly for those with low left ventricular ejection fractions.

The ability of the microprocessor to maintain a desired D/S Ratio would also be useful in the repetitive treatment of Stable Angina and CHF. In addition to maintaining a desired D/S Ratio throughout the one-hour or longer ECP treatment, when the patient returns for a subsequent ECP treatment, the microprocessor can recall the desired D/S Ratio from an inputted patient identification number or recognized from a patient dedicated compact disk or other electronic record, saving nursing time.

In another preferred embodiment of the ECP device of the present invention, in the treatment of CHF, a multi-function sensor can be attached to a mask over the patient's nose and mouth, the air tube of a mouthpiece fastened about the patient's head or an intubation tube inserted into the patient's airway. The multi-function sensor, by wires or telemetry, as known in the art, can transmit data to the microprocessor on the metabolic and cardiopulmonary functions of the patient, such as ventilatory efficiency/volume of C02 (VE/VC02), oxygen volume (V02), end title C02 (ETC02), volume of C02 (VC02), respiration rate and other indices. The microprocessor can use the data, along with the patient's blood pressure, obtained from the plethysmograph, and the heart rate and heart rate trend, obtained from the patient's ECG, to change the amount of pressure applied to the bladders of the cuffs and/or the time period during diastole that pressurization is commenced and the duration of compression, maintaining a desired D/S Ratio.

ECP produces a number of beneficial effects. These include (a) increasing blood flow and pressure in the arteries of the heart, causing the release of angiogenic factors and the growth of new blood vessels, (b) causing the release of nitrous oxide, a natural vasodilator; and (c) improving endothelial compliance (elasticity) of blood vessels. These effects are well known.

Other important beneficial effects of ECP, which have not been elucidated, include ECP's (a) "training effect" on the heart, particularly in persons suffering from congestive heart failure with low left ventricular ejection fractions, causing the chambers of the heart to beat in better synchrony and gradually accept and eject a greater volume of blood; (b) improving myocardial (heart muscle) contractility, enabling the heart to compress more efficiently; (c) increasing blood flow to the brain and nerves, improving synaptic efficiency of the brain's neurons and the vitality and transmission of signals by the nervous system; (d) increasing the flow of blood to the lungs, kidneys, liver and other organs, increasing shear force and improving oxygen transport and waste clearance; and (e) increasing blood flow to the glands of the endocrine system, improving their functionality.

The combination of the above known and, until now, unexplained benefits of ECP enable ECP to be beneficial in the treatment of a variety of conditions, which are described below and elsewhere in this application.

In three patients, a tiny pressure transducer (Millar Instruments, Inc. of Houston, Tex.) was placed in a coronary artery and when ECP was applied, intra-coronary artery pressure was increased up to 40%. This is deemed to be sufficient pressure to cause the release of angiogenic growth factors, such as a fibroblast growth factor (FGF), a vascular endothelial growth factor (VEGF) and others, which cause new vessels, usually capillaries and/or arterioles (small arteries), to form and grow around the blockage.

Only very small amounts of such growth factors are stored in depots in the artery wall. After about one hour of ECP, most or all of the stored growth factors are released. As a result, allowing about 12 to 24 hours between one hour applications of ECP gives the body time to produce these growth factors and re-stock the depots.

Consequently, in treating Chronic Angina, ECP is applied at high D/S Ratios (typically $\geqq$1.5 to 1) to cause the release of these growth factors. One hour of ECP is typically administered each day, five days a week (weekends off, because of the lack of skilled personnel in hospital outpatient departments, and cardiologists' offices typically being closed on weekends), until a total of 35 hours of more of ECP have been administered.

However, in the treatment of Acute Myocardial Infarctions (heart attacks), while ECP is typically applied at the same high D/S Ratios ($\geqq$1.5 to 1) as in the treatment of Angina, a different ECP regimen is used. In a published study (Amsterdam, et al, Am. J. Cardiol., 1980), heart attack victims received 4 hours of ECP, with a 10 minute rest period after each hour of ECP, to increase intra-coronary artery pressure and force blood through the collateral (secondary, often dormant) vessels around the blockage. After about four hours of ECP, blood flow to the area of the heart fed by the blocked vessel was able to reverse or reduce the damage to the heart wall caused by the lack of oxygen. In this study, 4 hours of ECP in the treatment of heart attack patients within 24 hours of the onset of symptoms reduced mortality by more than 56% from 14.7% to 6.5%. Four hours of ECP proved better than 2 hours, while 6 and 8 hours of ECP produced no added benefit.

We have discovered that continuing the application of ECP, after the initial 4 hours of ECP, at the rate of one hour of ECP each 12 or 24 hours, until a total of about 40 hours of ECP has been administered, is a preferred regimen for ECP in the treatment of heart attacks. In addition to the initial 4 hours of ECP's reducing the damage to the heart muscle, continued, periodic application of ECP provides the additional benefit of the release of angiogenic growth factors and the production of new vessels. These new vessels increase the supply of blood to the areas of the heart that may be still experiencing reduced blood flow, even if balloon angioplasty or bypass surgery is performed, which are only able to treat blockages in the 3 or 4 major coronary arteries.

We have discovered that applying about 4 hours of ECP before percutaneous transluminal coronary angioplasty ("PTCA") commonly referred to as balloon angioplasty, or coronary artery bypass graft (CABG) surgery and, commencing 12 to 24 hours after the PTCA procedure or 48 to 96 hours after the CABG procedure, continuing to apply ECP at the rate of one hour of ECP about each 12 or 24 hours thereafter, until a total of about 40 hours of ECP have been administered, can both perfuse and strengthen the heart as a result of the initial 4 hour ECP application, and cause the release of angiogenic growth factors and angiogenesis, as a result of the continued, periodic applications of ECP.

In a published study (Appelbaum, et al, American Heart Journal, 1997) Doppler ultrasound imaging was used during the application of ECP, and an increase of about 20% in both intra-carotid artery pressure (which arteries supply the brain) and renal artery pressure (which arteries supply the kidneys) was seen. Perfusing the brain enables it to better withstand the oxygen deprivation that may result during inflation of the balloon during angioplasty, or if the heart is stopped and the patient is put on a heart/lung machine during bypass graft (CABG) surgery.

We have discovered that ECP, applied in the regimen typically used to treat Chronic Angina, as described above, can be used to treat persons who suffered an ischemic stroke a few days or weeks earlier (ECP is contra-indicated in cases of hemorrhagic stroke) or who suffer from peripheral edema, retinal ischemia, erectile dysfunction, peripheral artery disease, chronic kidney failure or end stage renal disease, hepatic (liver) failure, diabetes and hypertension; cardiac nerve conduction conditions such as atrial fibrillation, ventricular fibrillation and ventricular tachycardia; pulmonary conditions such as emphysema, chronic obstructive pulmonary disease and pulmonary edema; and nervous system conditions such as epilepsy, diabetic neuropathy, sleep apnea, insomnia, anxiety disorders, depression, migraine headaches, senile dementia, cognitive deficits, Alzheimer's disease and Parkinson's disease, due to the release of angiogenic growth factors and increased blood flow to the heart, brain, lungs, pancreas, kidneys and other internal organs, nerves, glands and penis, as well as preventing deep vein thrombosis by moving blood in and out of the major veins.

We have also discovered that ECP applied in the regimen typically used to treat heart attacks, as described above, can also be used to treat acute ischemic strokes, acute renal failure and septic shock, which is now called multiple organ failure. The initial 4 hour ECP regimen perfuses the heart, kidneys, brain, nerves and internal organs, and the continued application of ECP causes the release of angiogenic growth factors and the creation of new blood vessels, as described heretofore.

To treat septic shock, if the patient's heart is strong, evidenced by a left ventricular ejection fraction (LVEF) greater than at least about 50%, ECP is best applied during systole, compressing the calves, thighs and buttocks sequentially, toward the heart. If the septic shock patient has an LVEF less than about 50%, ECP is best applied in the regimen for treating a heart attack, in the same sequence as described above, but during diastole, so as not to cause pressure against a weak heart's compression.

Likewise, we have discovered that the ECP regimen described above to treat heart attacks can be used to treat acute congestive heart failure (CHF), and the ECP regimen described above to treat chronic Angina can be used to treat chronic CHF, but with an important difference in both cases. If the CHF patient has a LVEF less than about 40%, ECP is applied in both acute and chronic CHF at D/S Ratios of about 0.7 to 1 for the first 5 hours of ECP (lower for very low LVEFs), increasing to 0.8 to 1 for the next 5 to 10 hours of ECP (lower for very low LVEFs) and increasing to 0.9 to 1 or 1:1 for the balance of the 35 hour ECP regimen, enabling the heart to gradually eject a greater volume of blood. If the ejection fraction is 40% to 50%, the D/S Ratio after the first 10 to 15 hours of ECP should not exceed 1.3 to 1, preferably not more than 1.2 to 1.

ECP also increases blood flow to nerves, improving their vitality and conduction (transmission) of signals, and to the brain, increasing the synaptic efficiency of neurons in the brain, making ECP beneficial in the treatment of the above brain and nerve related conditions, as well as in the treatment of atrial fibrillation, ventricular fibrillation and ventricular tachycardia (excessively fast heart beats), due to nerve conduction deficits or failures. ECP's aggressively moving blood out of the legs makes ECP valuable in the prevention of conditions such as deep vein thrombosis, and in the treatment of peripheral vascular disease, peripheral edema and diabetic neuropathy.

As described above, ECP is also beneficial in the treatment of cardiac arrest by supplementing manual CPR by returning the blood from the extremities to the heart; compressing the chest, alternating with compression of the extremities or, the latter with forcing air into the patient's lungs.

Numerous other variations of the principles of the present invention may be employed to treat other conditions by actuating the valves inflating the bladders of any or all of the cuffs at such times, at such pressures, and in any desired sequence during either diastole or systole. The invention may be described with greater clarity and particularity by reference to the accompanying drawings.

The present invention avoids the need to fully refill the hoses with pressurized air when the valves mounted on the bladders open and exhaust air into the atmosphere.

The present invention enables any or all of the individual bladders to be inflated for any selected time period during the cardiac cycle, for example, during either diastole or systole.

The present invention enables any or all of the individual bladders to be inflated in any desired sequence, toward the heart or toward the feet.

The present invention enables the time interval between the inflation of any of the individual bladders to be varied.

The present invention enables a selected amount of air pressure to be maintained in the bladders of any or all of the cuffs after the valves mounted on the bladders open and exhaust air into the atmosphere, taking up any empty space, thus requiring less air pressure and time to be consumed during the next cycle to produce the desired therapeutic effect.

The present invention enables the operator to command the microprocessor to over-ride the default limits based on the time interval between the "q" and "s" waveforms of the patient's electrocardiogram (ECG), to enable patients, for example, with a pacemaker or very slow or fast heart rate to be treated.

The present invention enables the operator to select a peak diastolic to peak systolic pressure ratio which the microprocessor will maintain by adjusting the inflation pressure of the bladders and/or the duration of inflation and the delay of inception of inflation from the "r" wave of the patient's ECG, enabling CHF or stable angina patients to be more effective effectively treated.

The present invention enables avoiding excessive preloading of CHF patient's hearts by limiting the peak diastolic to peak systolic pressure ratio.

The present invention enables ECP therapy for CHF patients to be optimized by separating the ECP treatments by more than one day.

The present invention enables the legs and buttocks of a person in cardiac arrest to be compressed for selected time periods and therapeutic pressures in the absence of an ECG signal.

The present invention enables the bladders of a chest cuff to be inflated, alternating such inflations with inflations of the bladders of the calf, thigh and/or buttocks cuffs; both for selected time periods, to treat a person in cardiac arrest and having no usable ECG signal.

The present invention enables air to be infused through a mouthpiece, intubation tube or mask into the lungs of a person in cardiac arrest for a desired time period at desired time intervals.

The present invention enables the inflation pressure, duration of inflation and/or delay in the time of inflation of the bladders from the "r" wave of a CHF patient's ECG to be automatically adjusted, based upon blood pressure, heart rate and pulmonary data from a sensor in a mouthpiece attached to the patient.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate at least one embodiment of the present invention. In such drawings.

DETAILED DESCRIPTION OF THE INVENTION

The above described drawing figures illustrate the invention in at least one of its preferred embodiments, which is further defined in detail in the following description.

Figure 1:
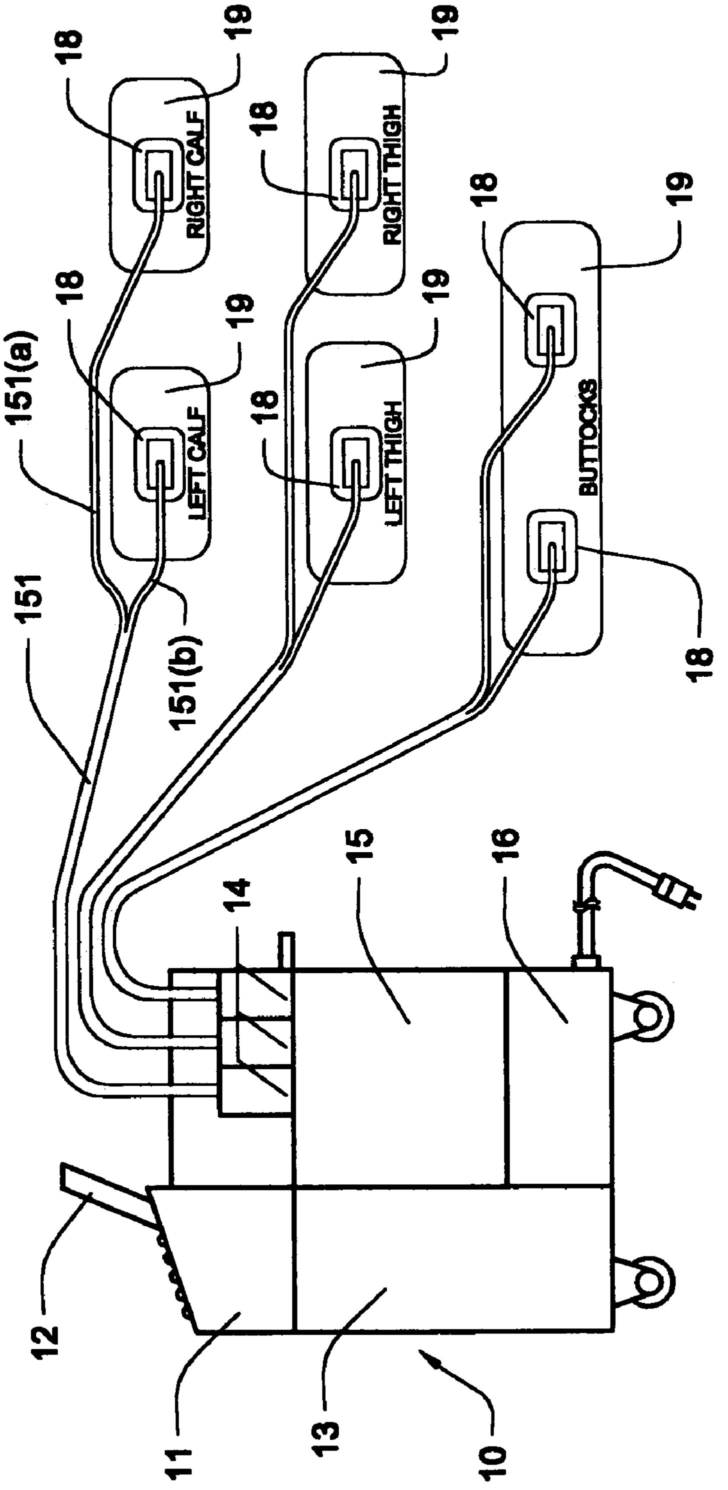
FIGURE 1 PRIOR ART
FIG. 1 is an elevational schematic diagram of a prior art ECP device.
Figure 2:
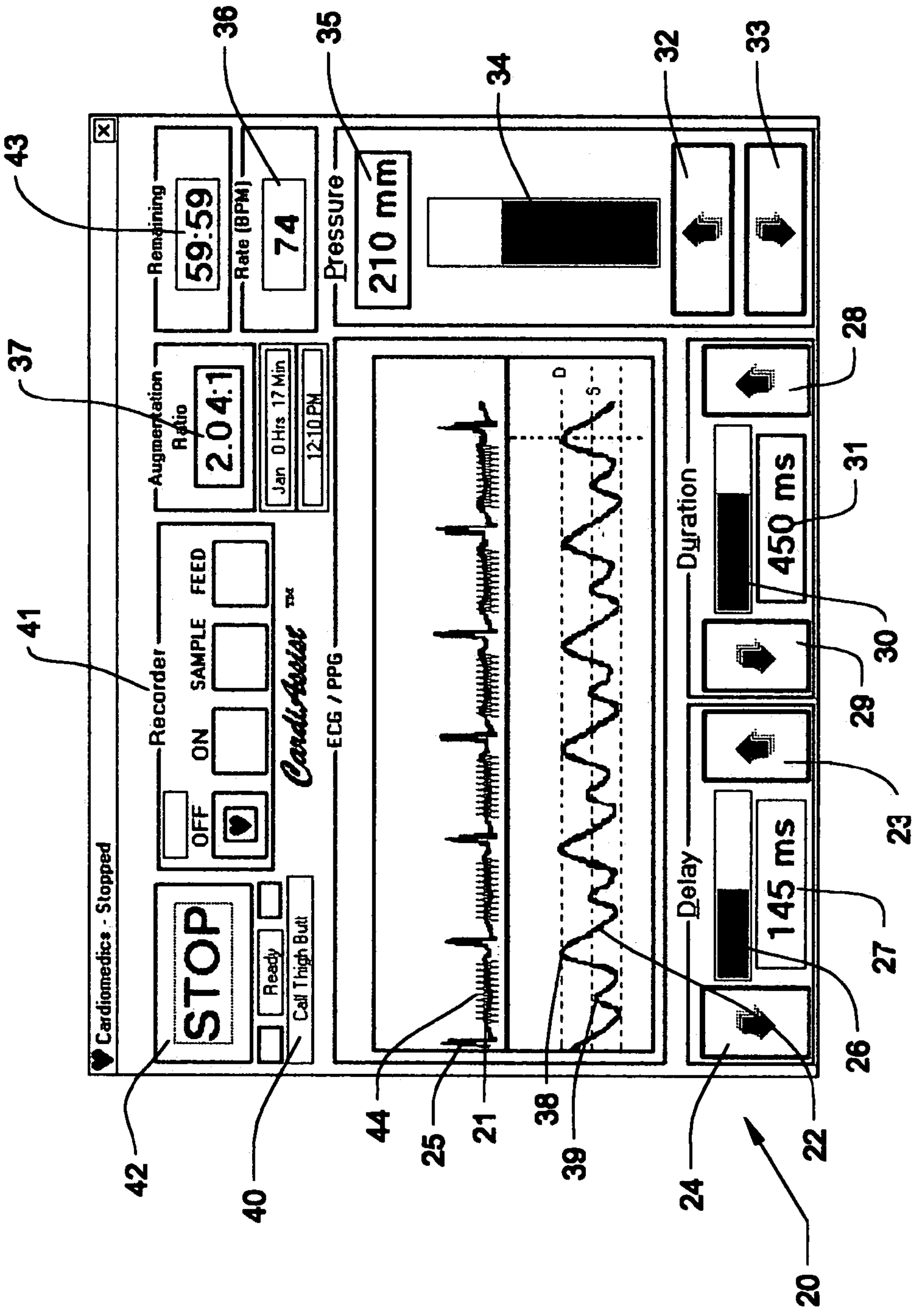
FIGURE 2 PRIOR ART
FIG. 2 is a diagram depicting a display screen thereof.
Figure 16:
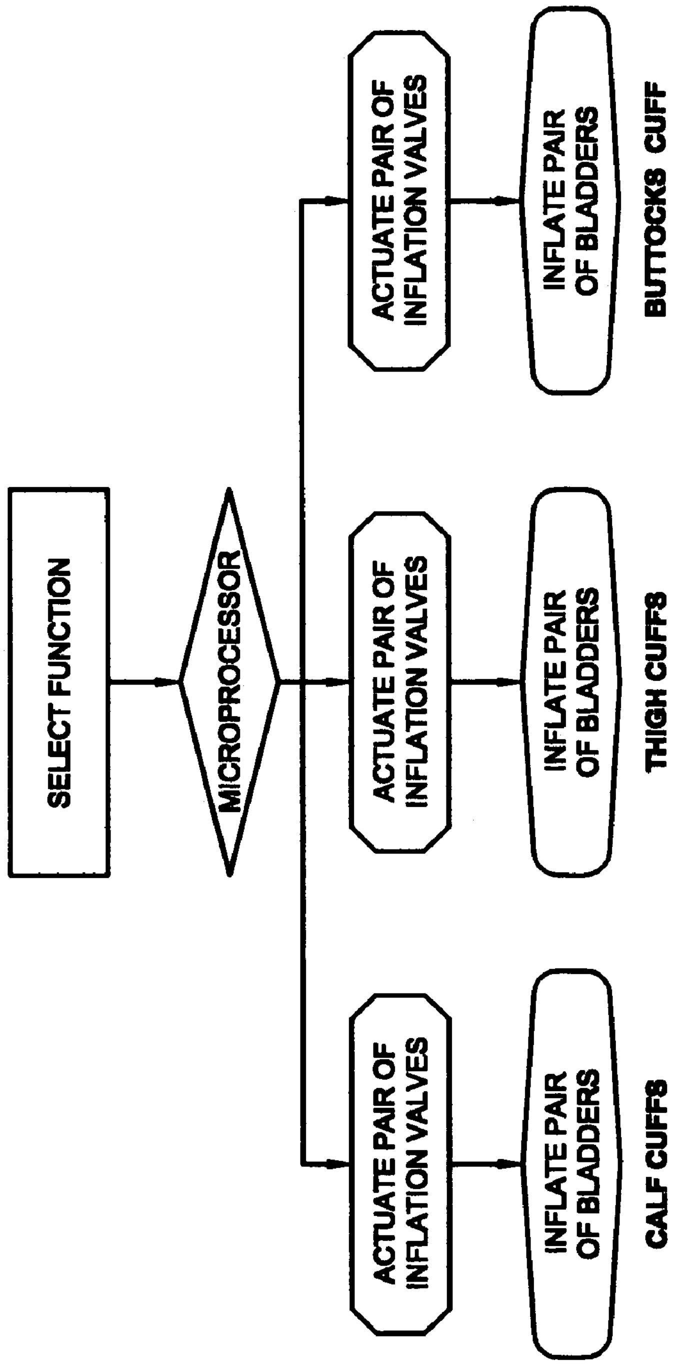
PRIOR ART FIGURE 16
FIG. 16 is a block diagram showing the elements of the prior art device.

The present invention is a ECP system, such as the prior art CardiAssist™ ECP System manufactured by Cardiomedics, Inc., of Irvine, Calif., and shown in FIGS. 1, 2 and 16. The ECP device 10 is comprised of a microprocessor 11 and associated electronic controls (not separately shown), touch screen display assembly 12, an air compressor compartment 13, containing one or more air compressors (not separately shown), solenoid valves 14 mounted on pneumatic reservoir 15, and power supply 16, along with a plurality of pneumatic hoses 151, which extend from solenoid valves 14, divide into pneumatic branch hoses 151(*a*) and 151(*b*), and are removeably attached to bladders 18 disposed within cuffs 19.

FIG. 2 illustrates a display screen 20 of a type used in the prior art, as seen on the touch screen display assembly 12 of the prior art ECP device of FIG. 1. As shown, display screen 20 shows the patient's ECG signal 21, obtained from ECG leads (not separately shown) removeably attached to the patient's chest, as known in the art, and the patient's blood pressure 22, obtained from a finger or ear plethysmograph device (not separately shown), as known in the art. In use, up arrow 23 and down arrow 24 are used to set the inception of compression of the cuffs, following an appropriate delay time from the 'Y' wave 25 of ECG signal 21, which is shown both as delay time bar 26 and in milliseconds on delay time display 27. Using up arrow 28 and down arrow 29, the duration of compression is set and shown both as duration time bar 30 and in milliseconds as duration time display 31. Using up arrow 32 and down arrow 33, the amount of air pressure to be applied to the bladders of the cuffs is shown both as pressure bar 34 and in millimeters of mercury as pressure display 35. The patient's heart rate 36 and augmentation ratio 37 (the ratio of peak diastolic pressure 38 to peak systolic pressure 39) are displayed. The order of compression 40, calf, thigh, buttock, in this case, is displayed. Strip chart recorder icons 41 enable a continuous or sample paper strip chart (not separately shown) of the patient's ECG and blood pressure and, optionally, the cuff compression period overlaid on the ECG pattern, to be printed out. Emergency stop icon 42 is provided for patient safety. The time of treatment remaining 43, counting down from 60 minutes, is also displayed. The period during which compression of the cuffs has been selected is displayed as wavy line 44 over the selected portion of ECG signal 21.

FIGS. 3-19 show the present invention, an improvement over the prior art device, which entails changes in the placement and actuation means of the inflation valves and the programming and functions of microprocessor 11.

Figure 3:
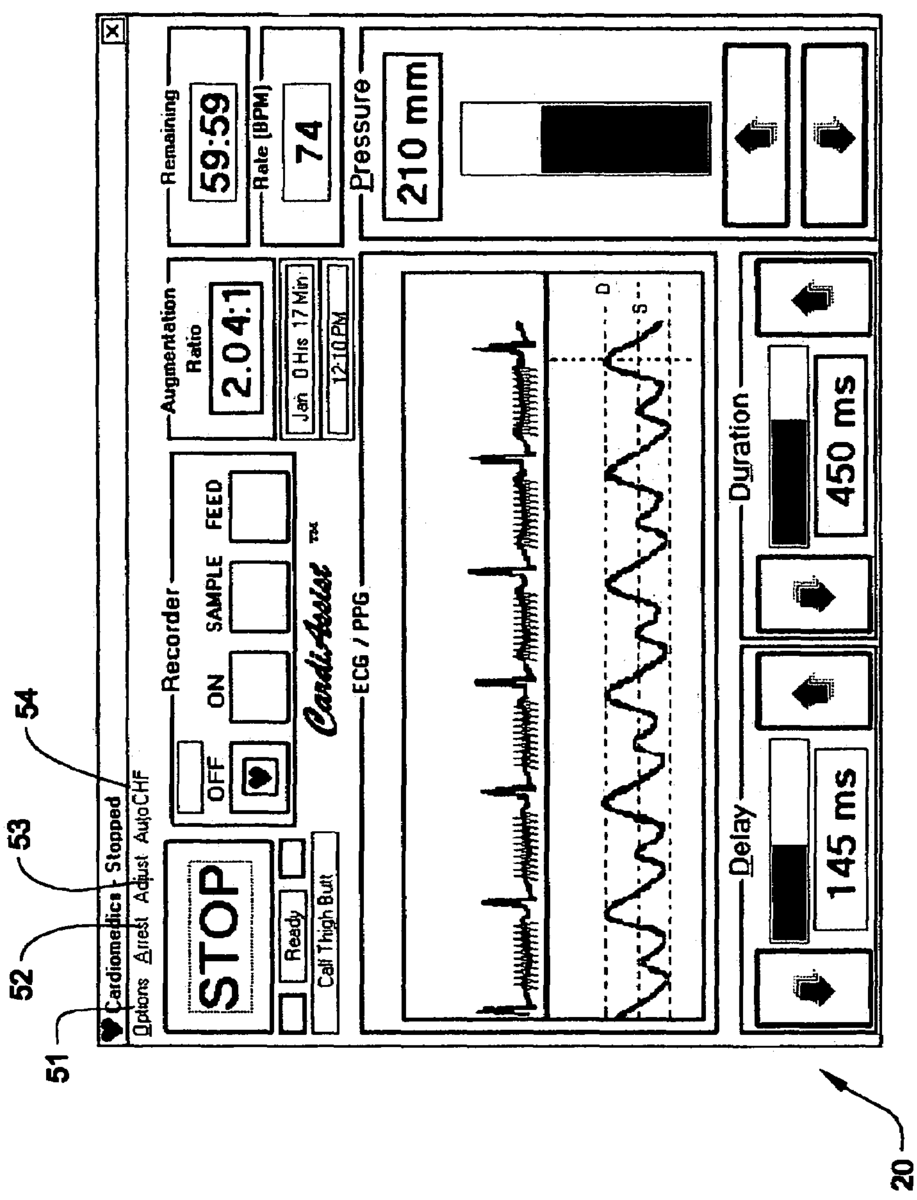
FIG. 3 is a diagram depicting a display screen of the present invention.

In the improvement shown in FIG. 3, in addition to all of the functions displayed on the display screen 20 of the prior art device in FIG. 2, the improved display screen 20 now contains the "Options" icon 51, the "Arrest" icon 52, the "Adjust" icon 53 and the "Auto CHF" icon 54. When the "Options" icon 51 is pressed, display screen 20 disappears and the drop-down compression menu 60, shown in FIG. 4, appears.

Figure 4:
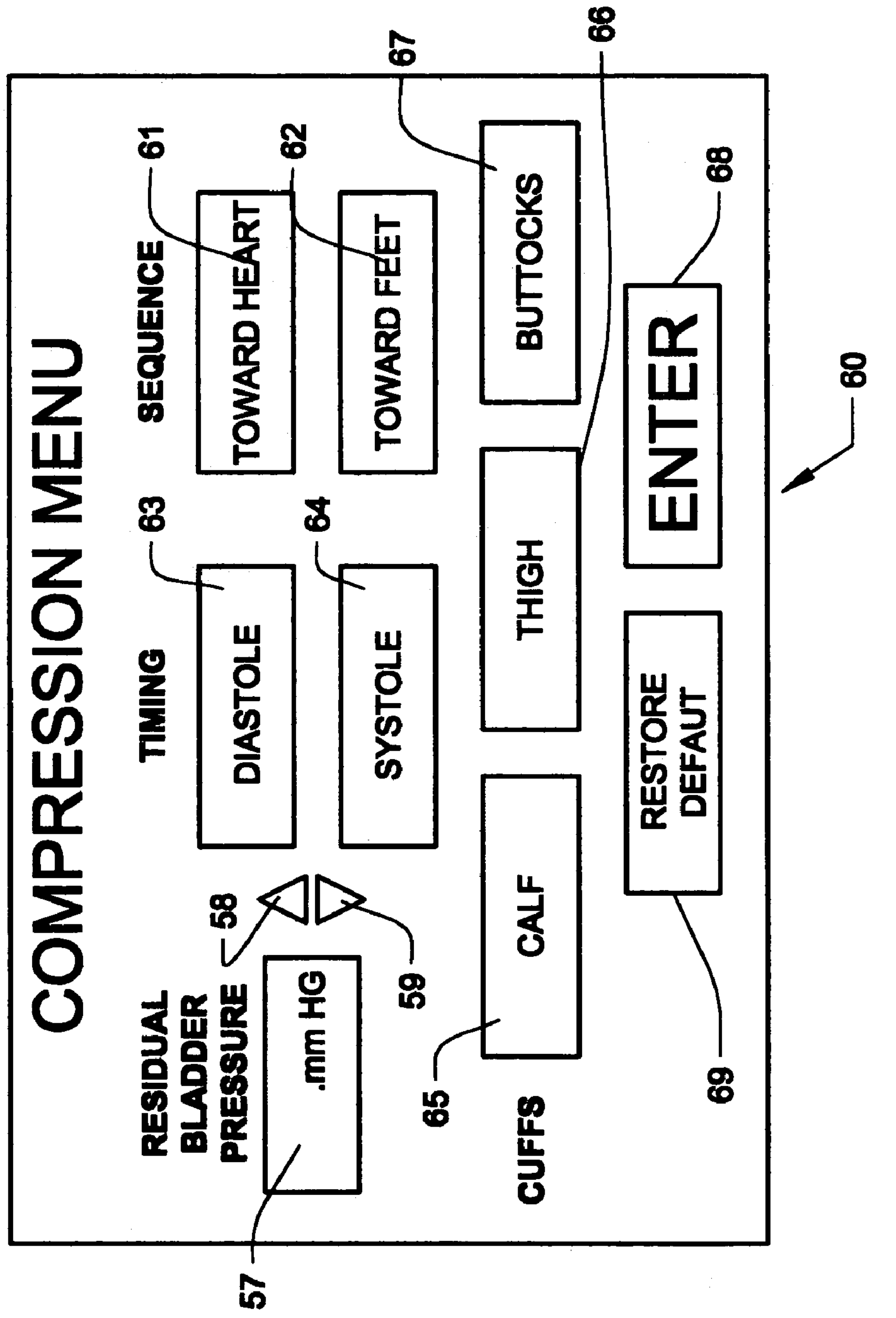
FIGS. 4-6, 8, 9 and 15 are diagrams depicting drop-down menus thereof.

As shown in FIG. 4, drop-down compression menu 60 enables the operator to select a residual bladder pressure to be maintained in the bladders 18 (FIG. 7) after their compression by pressing the "Residual Bladder Pressure" icon 57 and up arrow 58 or down arrow 59, respectively. Instead of completely deflating the bladders 18, a residual volume of air is retained in the bladders 18 between inflations to take up any space between the cuff and the portion of the body it encloses. However, the amount of residual air pressure is less than that which would create resistance to blood flow out of the heart, against the heart's compression during systole. In addition to reducing the time it takes to inflate the cuffs to the desired pressure, less air is lost when the cuffs are deflated, reducing the size and power requirements of the air compressor(s) of the ECP device. A residual air pressure of about 0.3 to 0.7 psi, preferably about 0.4 to 0.6 psi, may be retained in the cuffs, without significantly compressing the arteries of the extremities and causing resistance to pumping blood out of the heart on its next compression.

Alternatively, a pressure sensor mounted in each bladder or on each cuff may deliver, by wire or telemetry to microprocessor 11, data on the air pressure within each bladder of each cuff or the compression pressure of each cuff, and microprocessor 111 can cause each bladder 18 to be inflated to achieve a desired residual pressure. While the residual cuff pressure of, for example, 0.5 psi may generally be desired, it may be varied by the operator, as described above, based on the patient's height, weight or condition.

The operator may press the "Toward Heart" icon 61 or the "Toward Feet" icon 62 to select the sequence of inflation of the bladders 18 to compress the cuffs 19 (FIG. 7) in the desired direction. Likewise, the operator may cause compression of the cuffs 19 to occur (at the earlier selected pressure, delay time and duration selected by the operator) during either diastole or systole by pressing the "Diastole" icon 63 or the "Systole" icon 64. For patient safety, in the case of patients with coronary artery disease or impaired heart function, if the "Diastole" icon 63 is pressed, no matter what delay time from the "r" wave of the patient's ECG or compression duration period is selected by the operator, microprocessor 11 will not permit inflation of any of the bladders 18 during systole, which would exert force against the heart's next compression.

Also, the operator may press any or all of the "Calf", "Thigh" or "Buttocks" icons 65, 66 or 67, respectively, to select which pair of bladders 18 of cuffs 19 are to be inflated. For example, if the patient is to receive a femoral catheter, the buttocks cuff 19 may not be compressed and can be removed. If the buttocks cuff 19 is not employed, the insertion and use of a femoral catheter is facilitated, which is often required to monitor cardiac and other functions. If peripheral edema is to be treated, the sequence of the "Toward the Heart" icon 61 or the "Toward the Feet" icon 62 may be selected. For example, if septic shock is to be treated, compression of the cuffs 19 during systole may be selected by pressing the "Systole" icon 64.

Any or all of the individual icons are preferably illuminated when pressed. When the "Enter" icon 68 is pressed, those icons which were pressed and illuminated are no longer illuminated, the data is recorded by microprocessor 11, drop-down menu 60 disappears, and display screen 20, shown in FIG. 3, reappears. At any time during the use of drop-down menu 60, the operator may re-access display screen 20 by pressing the "Enter" icon 68. Optionally, the operator can restore the originally programmed values, called defaults, by pressing any or all of the individual icons 57-67 and pressing the "Restore Default" icon 69.

Figure 5:
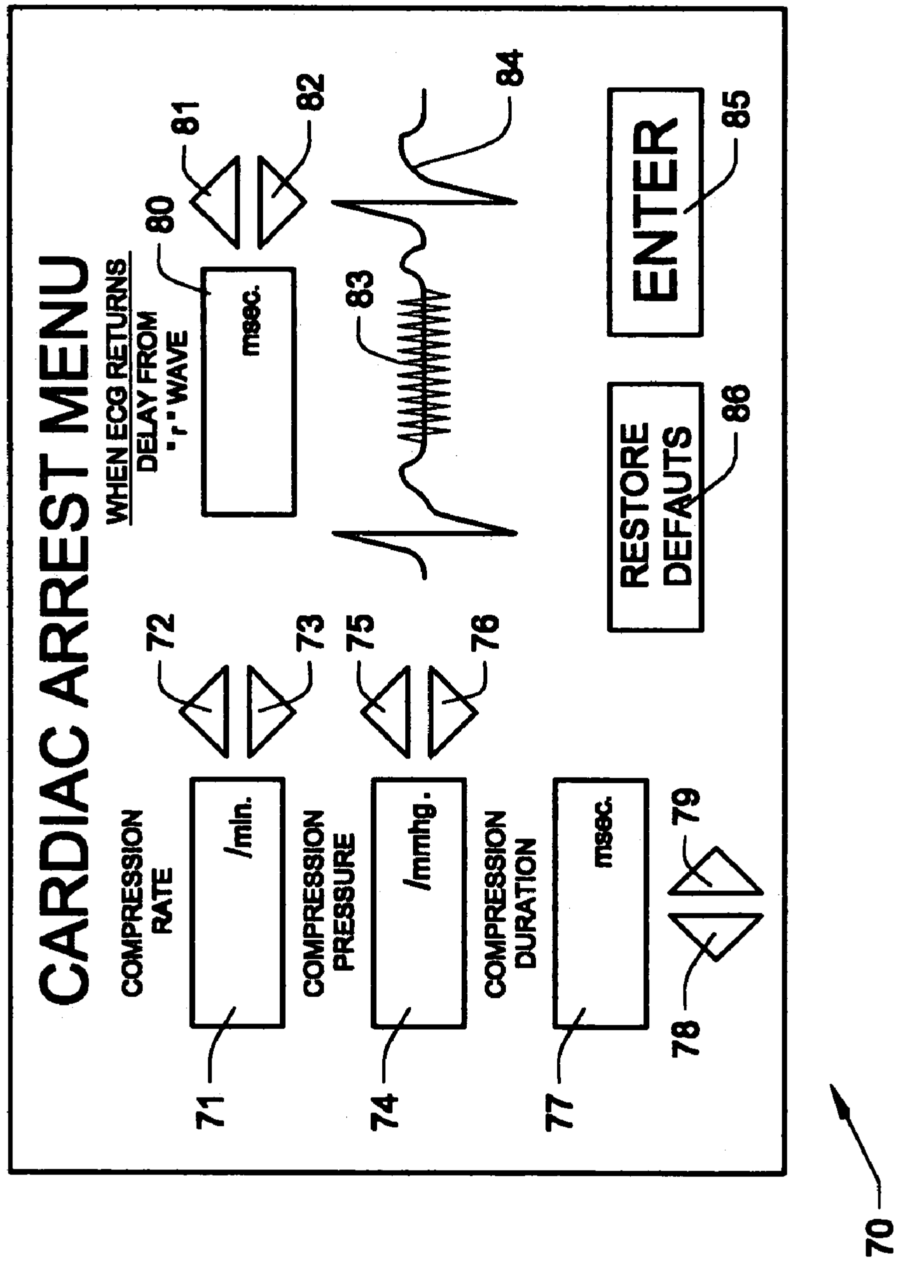

When the "Arrest" icon 52 of display screen 20 is pressed, drop-down "Cardiac Arrest Menu" 70, as shown in FIG. 5, appears. Drop-down "Cardiac Arrest Menu" 70 contains "Compression Rate" icon 71. When the "Compression Rate" icon 71 is pressed, the number of compressions per minute may be selected by pressing up or down arrows 72 or 73, respectively. Pressing the "Compression Pressure" icon 74, and up or down arrows 75 or 76, respectively, enables the pressure of compression to be changed and displayed in millimeters of mercury. Pressing the "Compression Duration" icon 77 and left or right arrows 78 or 79, respectively, changes and displays the duration period in milliseconds.

To prepare for the restoration of a normal heart rhythm, when an acceptable ECG signal is recognized by microprocessor 11, pressing the "Delay From 'r' Wave" icon 80 and up or down arrows 81 or 82, respectively, the delay time is changed and displayed in milliseconds. The duration of compression may be selected by pressing the. "Compression Duration" icon 77 and up or down arrows 78 or 79, respectively, and the duration of compression is shown as the wavy line 83 overlaid on the simulated ECG signal 84. When the operator is satisfied, the "Enter" icon 85 is pressed, and the selections are recorded by microprocessor 11, but display screen 20 of FIG. 3 does not re-appear. Defaults may be restored using the "Restore Defaults" icon 86.

When a normal heart rhythm returns, microprocessor 11 recognizes the restoration of an acceptable ECG signal, drop-down menu 70 disappears, the display screen 20 of FIG. 3 reappears, with the delay time from the "r" wave of the ECG, the compression pressure and the compression duration, selected as described in FIG. 5, are displayed, and the selected compression period is overlaid as a wavy line 83 on the patient's ECG. An audible alarm and/or a signal to the nursing station is preferably sent to alert a nurse to adjust the delay time from the "r" wave and duration of compression, based upon the patient's restored ECG signal and blood pressure pattern. If the patient's heart rhythm again becomes abnormal, microprocessor 11 recognizes the absence of an acceptable ECG signal, dropdown Cardiac Arrest menu 70 re-appears with the previously selected functions displayed, and compression of the cuffs resumes in accordance with the earlier selected values.

Figure 6:
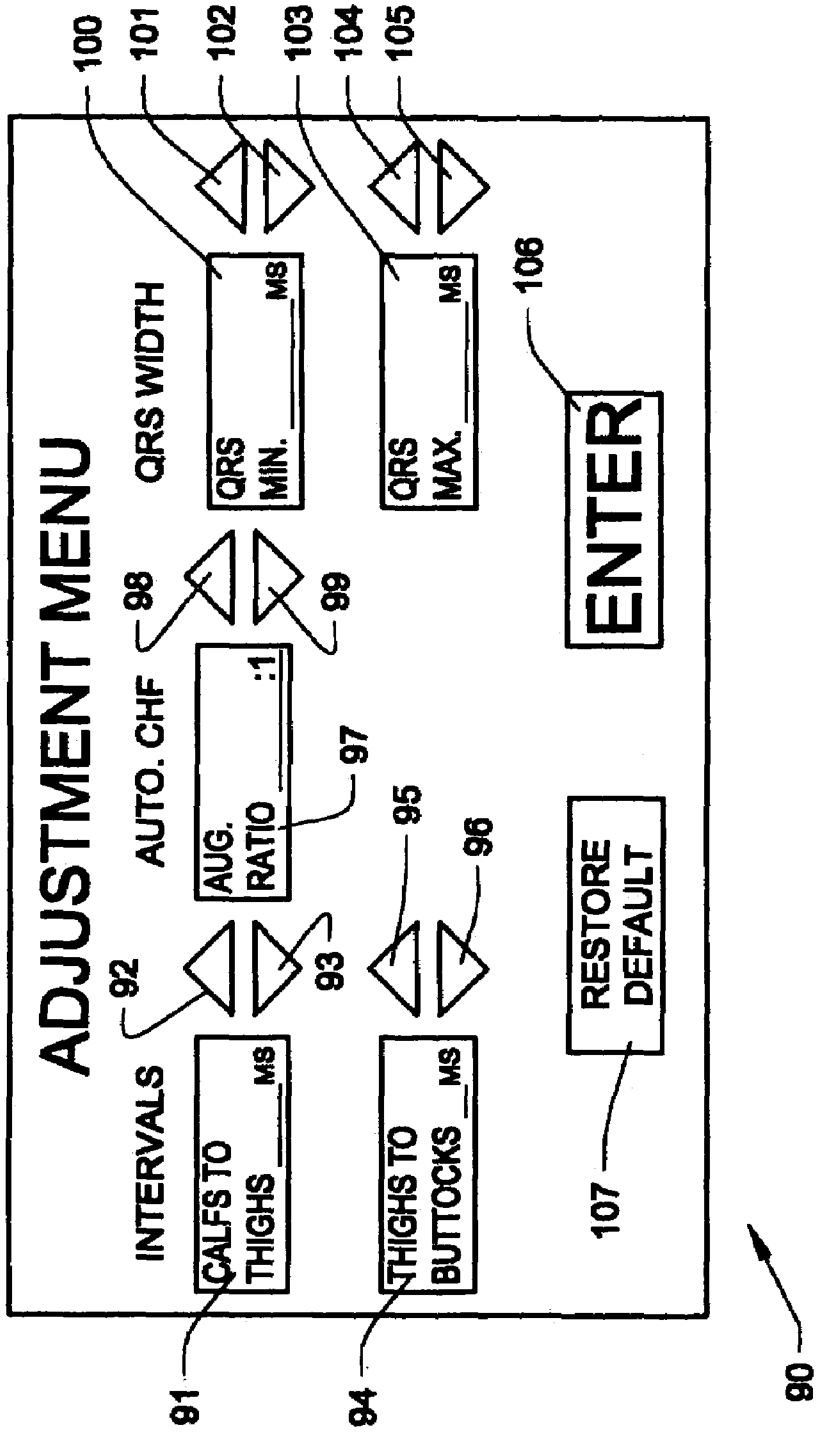

As seen in FIG. 6, when the "Adjust" icon 53 of FIG. 3 is pressed, display screen 20 disappears and drop-down Adjustment Menu 90 appears. The operator may adjust the originally programmed intervals between compression of the cuffs to a desired time. By pressing the "Calves to Thighs" icon 91 and up and down arrows 92 or 93, respectively, the time interval is changed and displayed in milliseconds. Likewise, by pressing the "Thighs to Buttocks" icon 94 and up or down arrows 95 or 96, respectively, the time interval is changed and displayed in milliseconds.

If the patient being treated is suffering from CHF and has a left ventricular ejection fraction less than about 40%, particularly for CHF patients with an ejection fraction less than about 30%, avoiding excessive pre-loading of the heart is desired. Pressing the "Auto CHF" icon 97 and up or down arrows 98 or 99, respectively, a desired peak diastolic pressure to peak systolic pressure ratio (D/S Ratio can be selected and displayed. If the patient's D/S Ratio exceeds or falls below the selected D/S Ratio, microprocessor 11 increases or decreases the inflation pressure of the bladders 18, without necessitating the constant attention of a nurse or technician. Optionally, microprocessor 11 can also be programmed to increase or decrease the delay time from the "r" wave of the patient's ECG and the duration of inflation of the bladders 18 to maintain the selected D/S Ratio.

This feature can also be utilized to maintain the desired D/S Ratio throughout the repetitive, one hour or, longer ECP treatments of a person with, for example, stable Angina, CHF or after a heart attack. Likewise, the patient's identification number can be inputted or recognized from a patient dedicated compact disc or other electronic record by microprocessor 11, which automatically causes the ECP device to produces the desired D/S Ratio during subsequent ECP treatments, saving nursing time.

If the patient has an HIS bundle block and a pacemaker has been implanted, or if the patient's ECG or heart rate is producing a "qrs" interval outside the normal "qrs" interval programmed into microprocessor 11, but is not producing typical premature ventricular contractions or PVC's, the operator may increase the acceptable minimum and/or maximum "qrs" interval. To do this, the operator may press the "QRS Min." icon 100 and up or down arrows 101 or 102, respectively, and the "QRS Max." icon 103 and up or down arrows 104 or 105, respectively, whereupon the selected minimum and/or maximum qrs widths are displayed in milliseconds. When pressed, the icons may be illuminated and the functions of the "Enter" icon 106 and the optional "Restore Default" icon 107 are as described with respect to FIG. 4.

Figure 7:
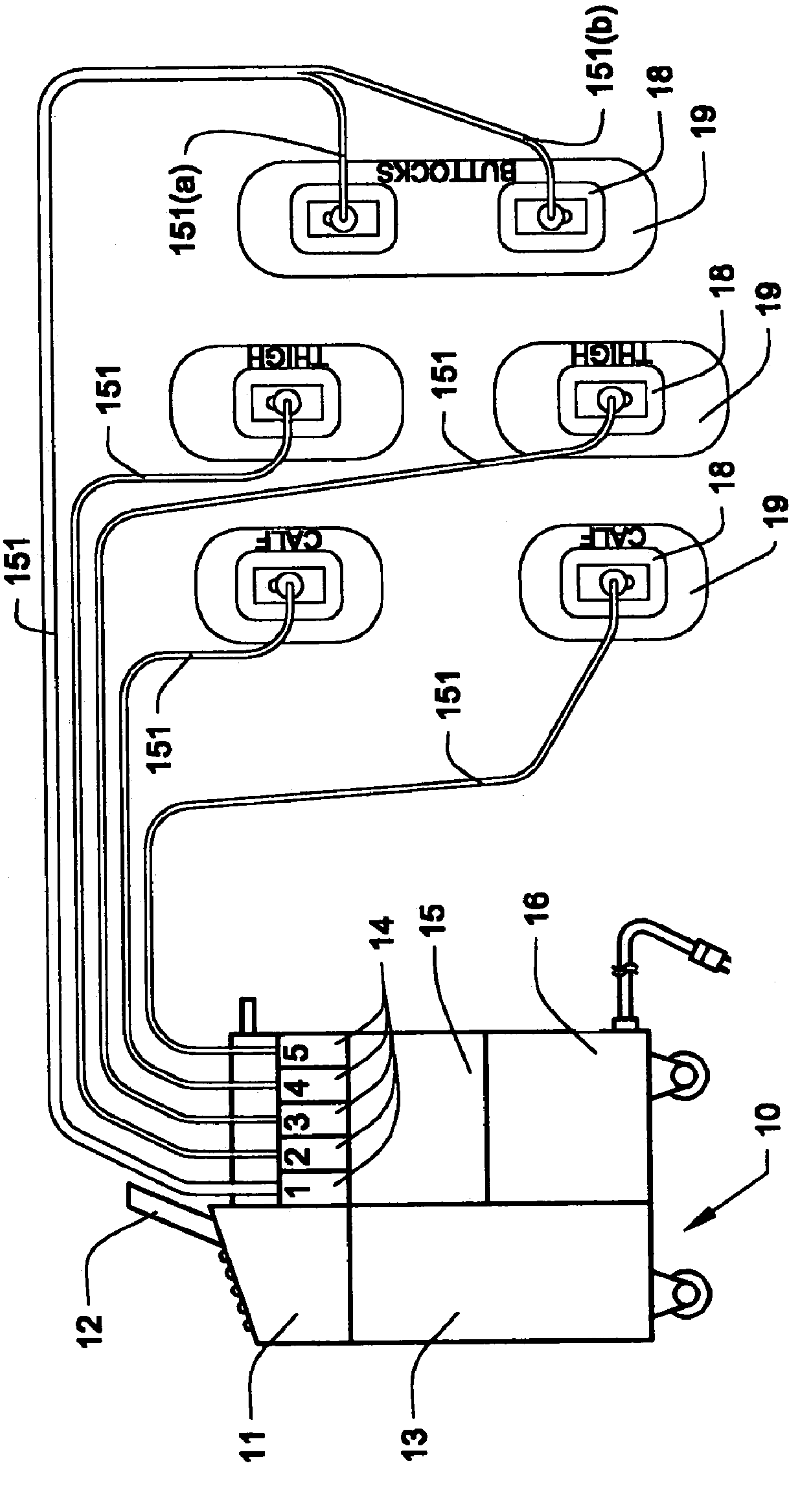
FIGS. 7, 10, 12 and 13 are elevational schematic diagrams showing preferred embodiments of the present invention, an improved ECP device.

FIG. 7 illustrates a preferred embodiment of the ECP device of FIG. 1. In this embodiment, at least five solenoid valves 14 are mounted on and in fluid communication with an air reservoir (not separately shown) in air reservoir compartment 15. A separate, main air hose 151, with an inside diameter of preferably between 1.5 to 2 inches, extends from the first solenoid valve 14 and divides into two smaller branch air hoses 151(*a*) and 151(*b*), with inside diameters of preferably about 0.75 to 1.25 inches, and are removeably attached to bladders 18 within buttocks cuff 19. Separate, smaller diameter air hoses 151, with an inside diameter of about 0.5 to 1.5 inches, preferably about 0.75 to 1.25 inches, extend from the second to fifth solenoid valves 14 and are each removeably attached to one of the bladders 18 disposed within the respective left and right thigh and calf cuffs 19. Microprocessor 11 may be programmed to inflate any or all of the bladders of the cuffs for such time periods during the cardiac cycle, to adjust the inflation values to retain a selected residual pressure in any or all of the bladders or to compress any or all of the selected bladders 18 to a desired pressure chosen by the operator. Retaining air pressure in the bladders of the cuffs may take up empty space, requiring less air pressure to reach the therapeutic level. Also, limiting the amount of pressure in the bladders of certain of the cuffs may avoid pain and enable a person to be treated who is suffering from, for example, an injury to, gangrene or peripheral vascular disease in one leg.

Figure 8:
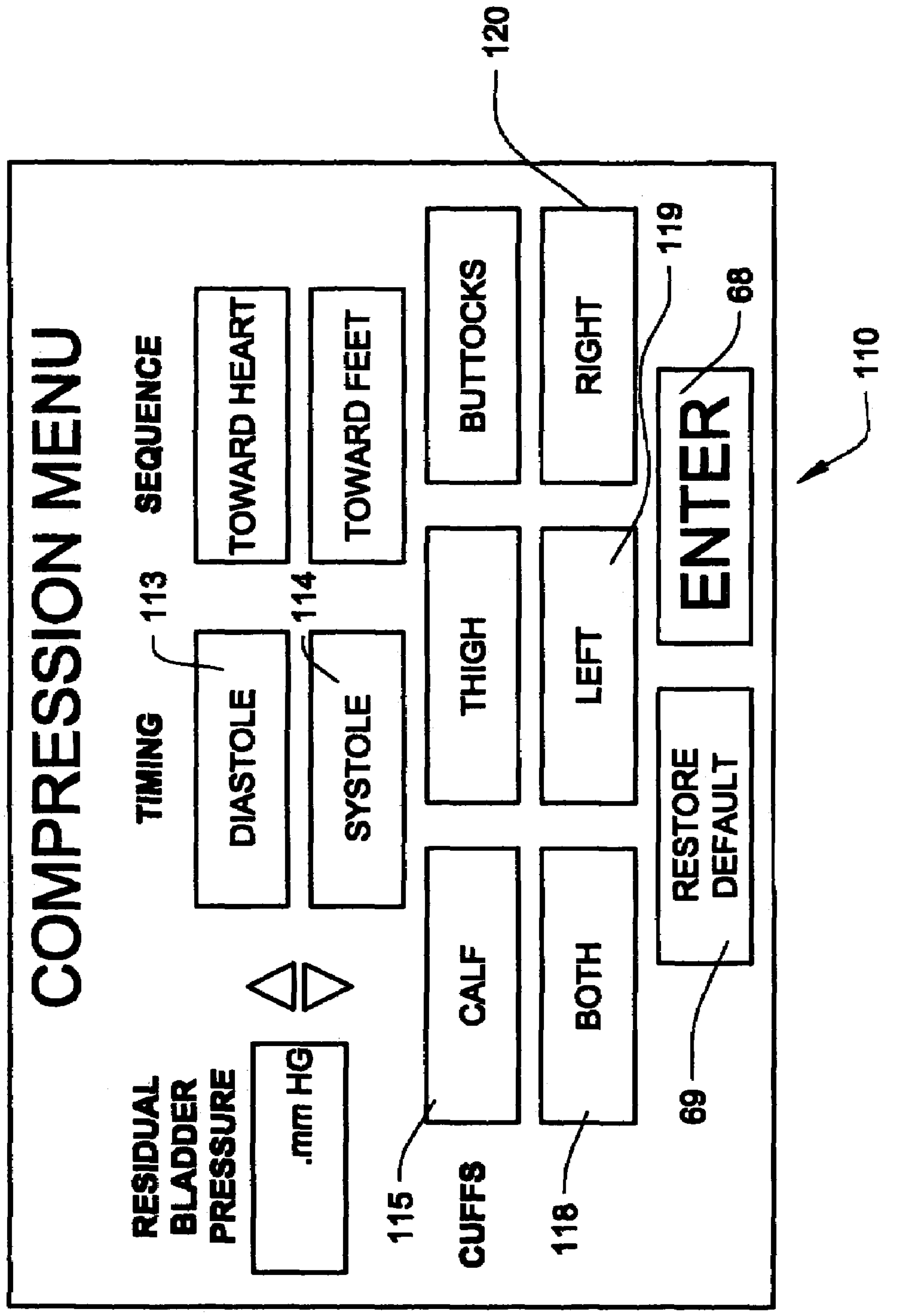

As illustrated in FIG. 8, in addition to the selections contained in drop-down Compression Menu 60 shown in FIG. 4, drop-down Compression Menu 110 of the device of FIG. 7 enables the operator to press the "Both" 118, the "Left" 119 or the "Right" 120 icons to inflate bladders 18. Alternatively, the "Both" icon 118 can be eliminated and, if both the "Left" icon 119 and the "Right" icon 120 are pressed, microprocessor 11 will cause the bladders 18 of both the left and right calf and thigh cuffs 19 to be inflated. When the operator is satisfied with his/her selections, the "Enter" icon 124 is pressed, the data is recorded by microprocessor 11, drop-down menu 116 disappears and display screen 20 of the device of FIG. 3 re-appears. Operation of the "Enter" icon 68 and the "Restore Default" icon 69 is as defined for FIG. 4.

Figure 9:
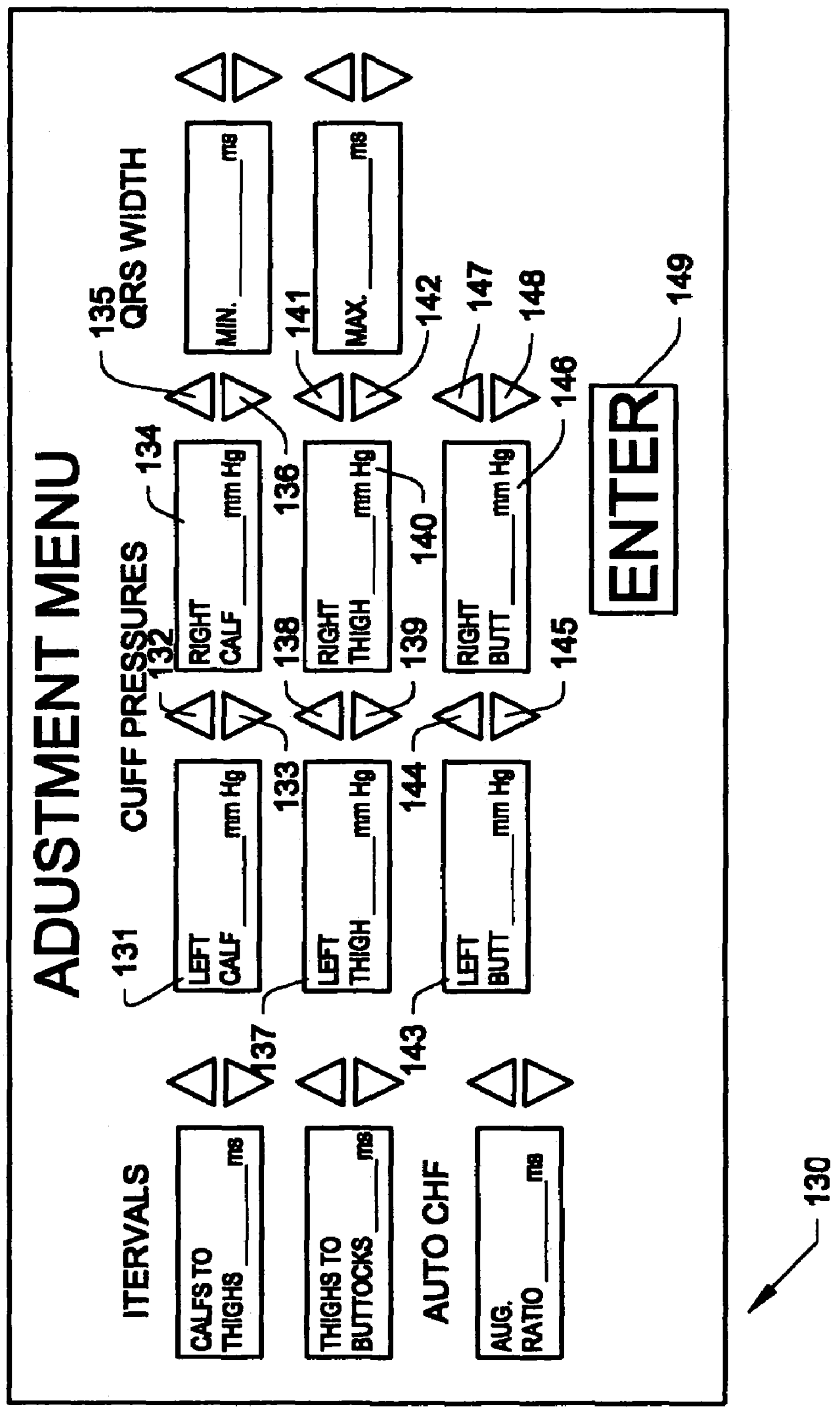

As illustrated in FIG. 9, in an alternate embodiment of the present invention, when the "Adjust" icon 53 of FIG. 3 is pressed, drop-down Adjustment Menu 130 may be caused to appear. In addition to the functions described in FIG. 6, the operator may adjust the compression pressure of the bladders 18 of any or all of the cuffs 19. By pressing the "Left Calf" icon 131 and up or down arrows 132 or 133, the "Right Calf" icon 134 and up or down arrows 135 or 136, the "Left Thigh" icon 137 and up or down arrows 138 or 139, the "Right Thigh" icon 140 and up or down arrows 141 or 142, the "Left Butt" icon 143 and up or down arrows 144 or 145 or the "Right Butt" icon 146 and up or down arrows 147 or 148, the amount of pressure in millimeters of mercury is selected and displayed for each bladder 18 and corresponding cuff 19 selected. If desired, an optional "Restore Default" icon (not separately shown) may be added. Again, the displays and icons are illuminated and, when the "Enter" icon 149 is pressed, the events occur as described above for FIG. 4.

Figure 10:
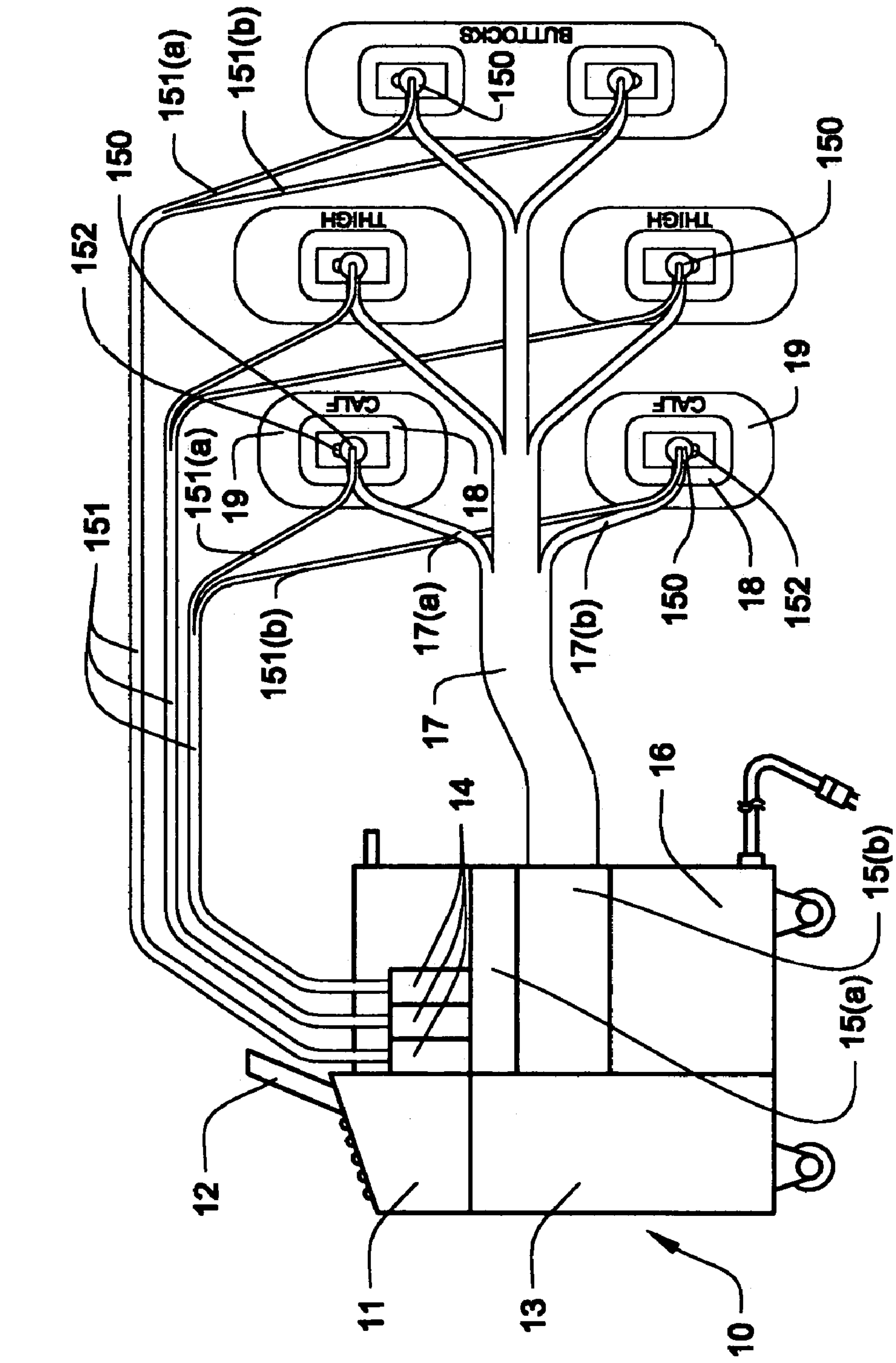

FIG. 10 shows diagrammatically, in a further preferred embodiment of the present invention, an advanced ECP system. In this embodiment, ECP device 10 is comprised of a microprocessor 11 and associated electronics (not separately shown), touch screen display assembly 12, an air compressor compartment 13, containing one or more air compressors (not separately shown), high pressure air reservoir 15(*a*), low pressure air reservoir 15(*b*) and power supply 16. A single, large diameter main air hose 17 emanates from low-pressure reservoir 15(*b*) and serves as a pneumatic trunk line. Main air hose 17 branches into smaller diameter branch air hoses 17(*a*) and 17(*b*), each of which serve as a separate branch pneumatic supply line. Each of the branch hoses 17(*a*) or 17(*b*) extends to and is removeably attached to a separate one of a plurality of an APA type individual air actuated inflation valves 150, each of which is attached to the inlet of one of separate bladders 18 disposed within separate cuffs 19, which are secured by, for instance, Velcro® type hook and loop surface fastening material about the patient's calves, thighs and/or buttocks. Main air hose 17 may have an inside diameter (I.D.) of between 1.5 and about 3 inches, and is preferably between 2.0 and 2.5 inches in diameter. Hose branch extensions 17(*a*) and 17(*b*) can have an I.D. of about 1 inch to 1.5 inches, preferably about 0.75 to 1.25 inches in diameter. Separate air pilot lines 151 extend from each of three solenoid valves 14 mounted on and in fluid communication with high pressure air reservoir 15(*a*). Each of air pilot lines 151 branches into two, smaller diameter branch air pilot lines 151(*a*) and 151(*b*), the distal end of each being removeably attached to one of the individual inflation valves 150. Each pilot line 151 typically has an I.D. of from about 0.125 to about 0.25 inch, and each branch air pilot line 151(*a*) and 151(*b*) typically has an I.D. of from about 0.0825 to about 0.1875 inch.

High pressure air reservoir 15(*a*) holds a supply of air under elevated pressure of about 12 to 30 psi, preferably about 16 to 26 psi. Low pressure air reservoir 15(*b*), main air hose 17 and air hose branches 17(*a*) and 17(*b*) hold a supply of air under elevated pressure, up to about 10 psi, preferably up to about 6 psi. Each of branch air hoses 17(*a*) and 17(*b*) is attached to one of the air-controlled valves 150 attached to the inlet of one of separate bladders 18 disposed in cuffs 19. High pressure reservoir 15(*a*) is preferably connected to low pressure reservoir 15(*b*) by a variable pressure or proportional valve (not separately shown) as known in the art, which is controlled by microprocessor 11 and enables high pressure reservoir 15(*a*) to "feed" air to low pressure reservoir 15(*b*) in an amount necessary to maintain the pressure commanded by microprocessor 11. Optionally, microprocessor 11 can adjust the pressures in reservoirs 15(*a*) and 15(*b*), based on signals from pressure sensors (not separately shown) contained in reservoirs 15(*a*) and 15(*b*) or air hose 17 and air pilot lines 151, respectively.

Air pilot lines 151 and branch air pilot lines 151(*a*) and 151(*b*) enable air released from high pressure reservoir 15(*a*) by solenoid valves 14 to actuate the opening and closing of the inflation/deflation mechanisms (not separately shown) of the valves 150. Using air through air pilot lines 151 and branch air pilot lines 151(*a*) and 151(*b*) to actuate valves 150, instead of using wires and electric current, avoids subjecting the patient to the possible risk of an electrical shock. In use, air pilot lines 151 and branch air pilot lines 151(*a*) and 151(*b*) may be attached to or bound together with main air hose 17 and branch air hoses 17(*a*) and 17(*b*), respectively, as known in the art. Exhaust ports 152 of air controlled valves 150 enable air from bladders 18 to be discharged into the atmosphere. Alternatively, a vacuum pump (not separately shown) may be used to draw air out from bladders 18 through vacuum hoses (not separately shown). Exhaust ports 152 may each contain an exhaust or check valve (not separately shown), as known in the art, which automatically closes when air pressure in their attached bladder 18 falls to a preferred level to retain a residual amount of air pressure in bladders 18.

Figure 11:
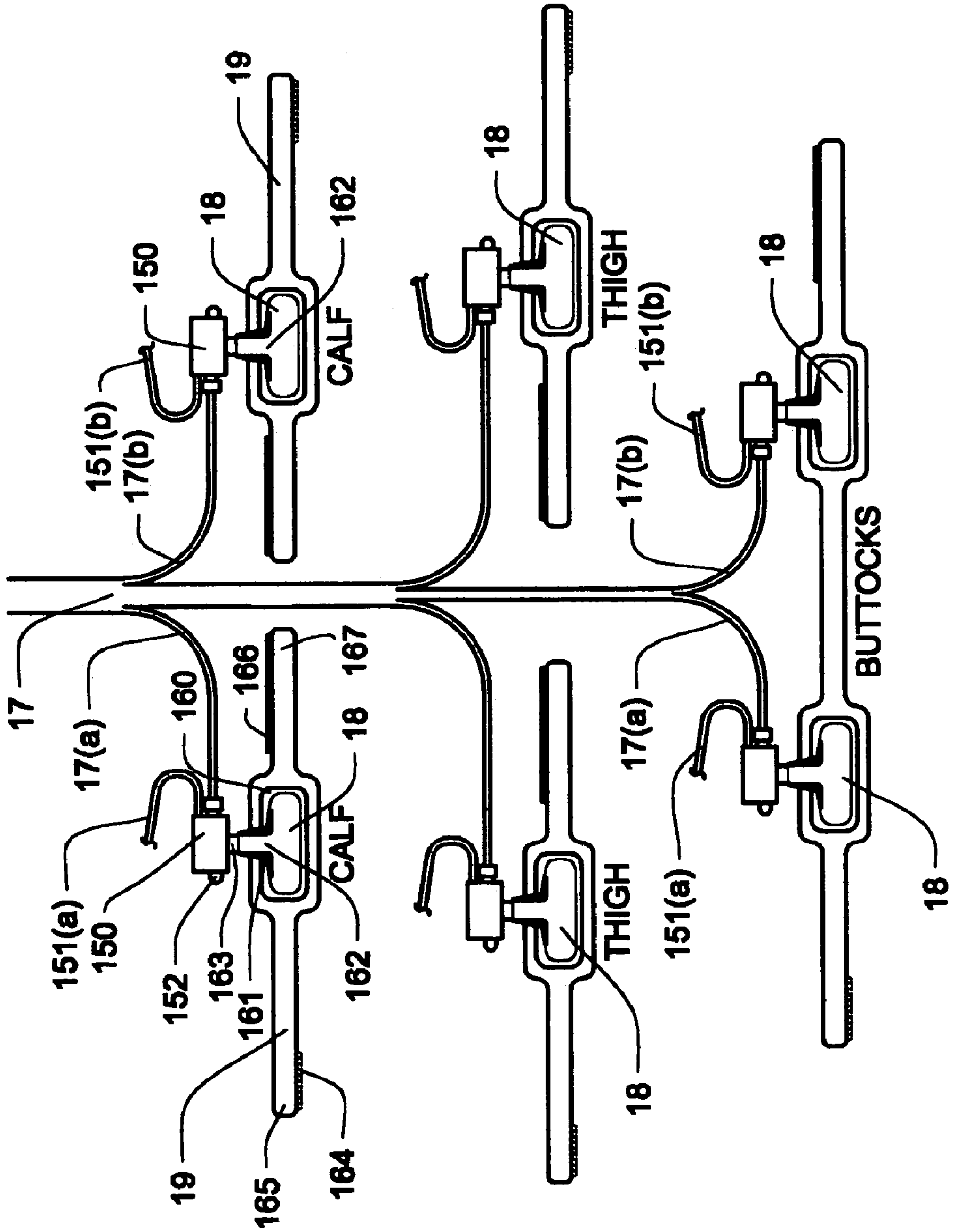
FIG. 11 is a plan view of cuffs, bladders and inflation valves thereof.

As seen in FIG. 11, each cuff 19 contains one or more enclosed cavities or pockets 160, within which a bladder 18 is disposed. Support 161 may be made of plastic or metal and is attached about inflation port 162 of bladder 18. While support 161 may be attached to the exterior of bladder 18 over port 162 by an adhesive or thermal fusion, in one preferred arrangement, support 161 is also preferably attached by an adhesive or thermal fusion to the interior surface of bladder 18, and extends through port 162, as illustrated. Support 161 may have an externally threaded nipple 163, onto which air controlled valve 150 may be threaded. Alternatively, air controlled valve 150 may be attached to nipple 163 by a quick disconnect connector, as known in the art.

A narrow Velcro® strip 164 is attached to the bottom surface of cuff end 165 of each cuff 19, and a wide Velcro® strip 166 is attached to the top surface of cuff end 167 of each cuff 19. Velcro® strips are manufactured by Velcro USA, Inc., of Manchester, N.H., and are attached to each cuff 19 by sewing them in place, by thermal fusing and/or an adhesive. In use, when cuff ends 165 and 167 are wrapped about a limb or the buttocks of a patient and are brought together, narrow Velcro strip 164 is removeably attached to wide Velcro strip 166. Wide Velcro strip 166 enables narrow Velcro strip 164 to be removeably attached to wide Velcro strip 166 at various points along its length, permitting cuffs 19 to be snugly secured to patients of different sizes.

Cuffs 19 may be made, for example, of a 600 dernier nylon material or a polycoated polyester. The tubing of trunk hose 17 and hose branches 17(*a*) and 17(*b*) can be made of wire or nylon cord-reinforced polyvinyl chloride. Hoses 17 and hose branches 17(*a*) and 17(*b*) can be smooth or corrugated, as desired. Each branch air pilot line 151(*a*) or 151(*b*) is attached to one of the air actuated valves 150. Air pilot lines 151(*a*) or 151(*b*) can be made, for example, of polypropylene tubing or any other suitable material, as known in the art.

Each air controlled valve 150 is actuated by air pressure through its attached branch air pilot line 151(*a*) or 151(*b*), which is actuated at a pressure of from about five to twenty psi, preferably about seven to fifteen psi. When activated by sufficient air pressure through branch air pilot line 151(*a*) or 151(*b*), air controlled valve 150 allows pressurized air from branch hoses 17(*a*) or 17(*b*) to fill its attached bladder 18. When the air pressure exerted through branch air pilot line 151(*a*) or 151(*b*) falls to between about zero to five psi, inflation air controlled valve 150 allows the air in its attached bladder 18 to exit through exhaust port 152. Hose branches 17(*a*) and 17(*b*) and branch air pilot lines 151(*a*) and 151(*b*) may be removably attached to their respective air controlled valve 150 by commercially available threaded connectors or quick connect devices, as known in the art.

Optionally, an air relief or check valve (not separately shown), as known in the art, can be attached to, or contained within each of exhaust ports 152 or, optionally, may be a component of each of the air controlled valves 150 and mounted on the inlets of bladders 18. The air relief valves close when the air pressure in its associated bladder 18 falls to a selected level to retain a desired amount of residual air pressure in bladder 18.

Figure 12:
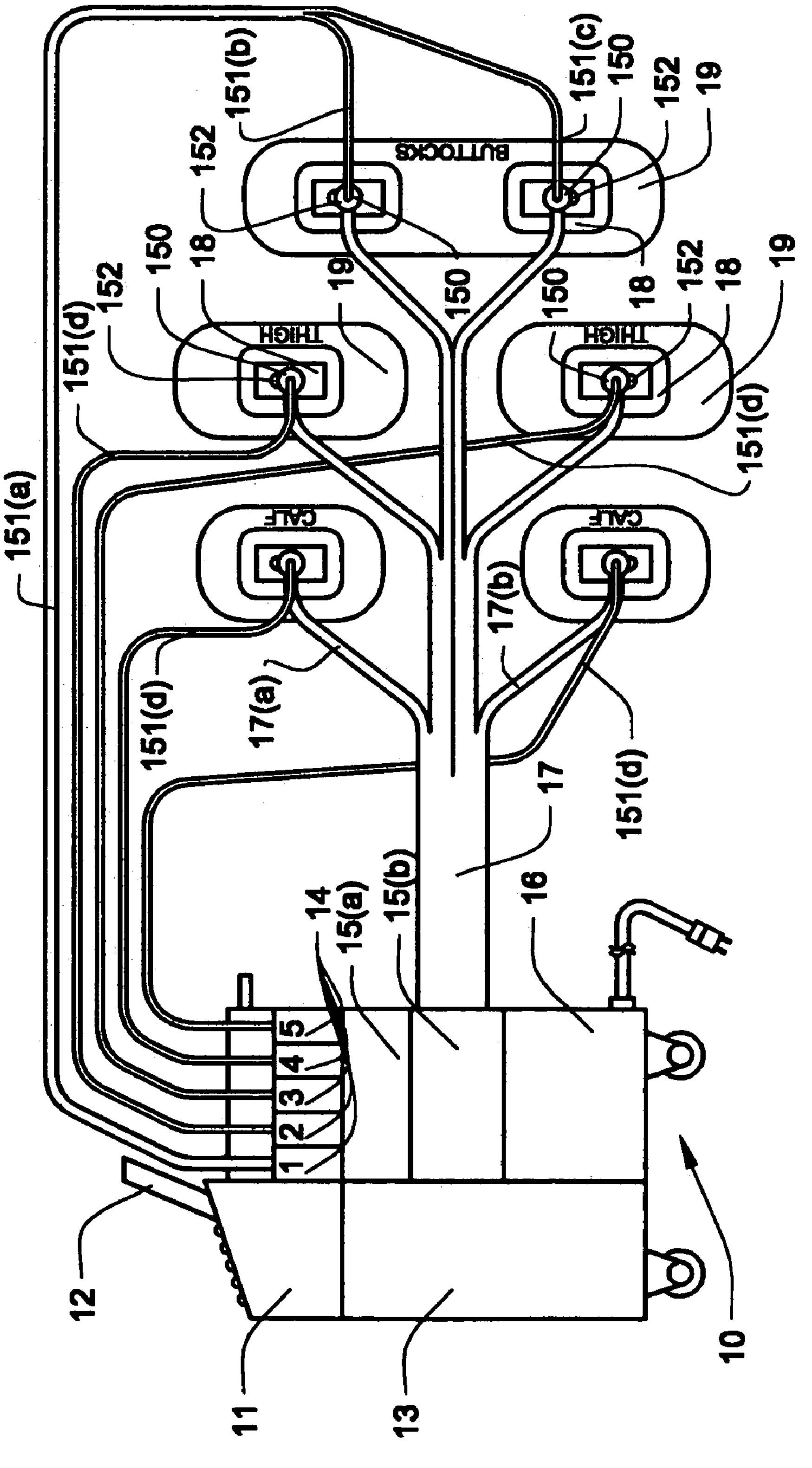

A preferred embodiment of the present invention is illustrated in FIG. 12. At least five solenoid valves 14 are mounted on and in fluid communication with high-pressure reservoir 15(*a*). One air pilot line 151(*a*) extends from the first solenoid valve 14 and branches into two branch pilot lines 151(*b*) and 151(*c*), which each extend to one of the two air controlled valves 150 mounted on the two bladders 18 of the buttocks cuff 19. An individual air pilot line 151(*d*) extends from each of solenoid valves 14 numbered 2-5 and are each removeably attached to one of air controlled valves 150 mounted on each of the four bladders 18 of the two calf cuffs 19 and the two thigh cuffs 19. The advantage of this preferred embodiment is that any or all of the air controlled valves 150 of the bladders 18 of the calf or thigh cuffs 19 may be actuated or not. For example, if the patient is an amputee, recently had a sapphenous vein removed from one leg for use in bypass surgery, for instance, or has a broken leg, the air controlled valve 150 of only the calf and thigh bladders 18 of the cuffs 19 of the healthy leg may be actuated. Also, the Air controlled valve 150 of the bladders 18 of the buttocks cuff 19 may or may not be actuated, if, for example, the patient is to receive a femoral catheter or balloon angioplasty, as described above.

Figure 13:
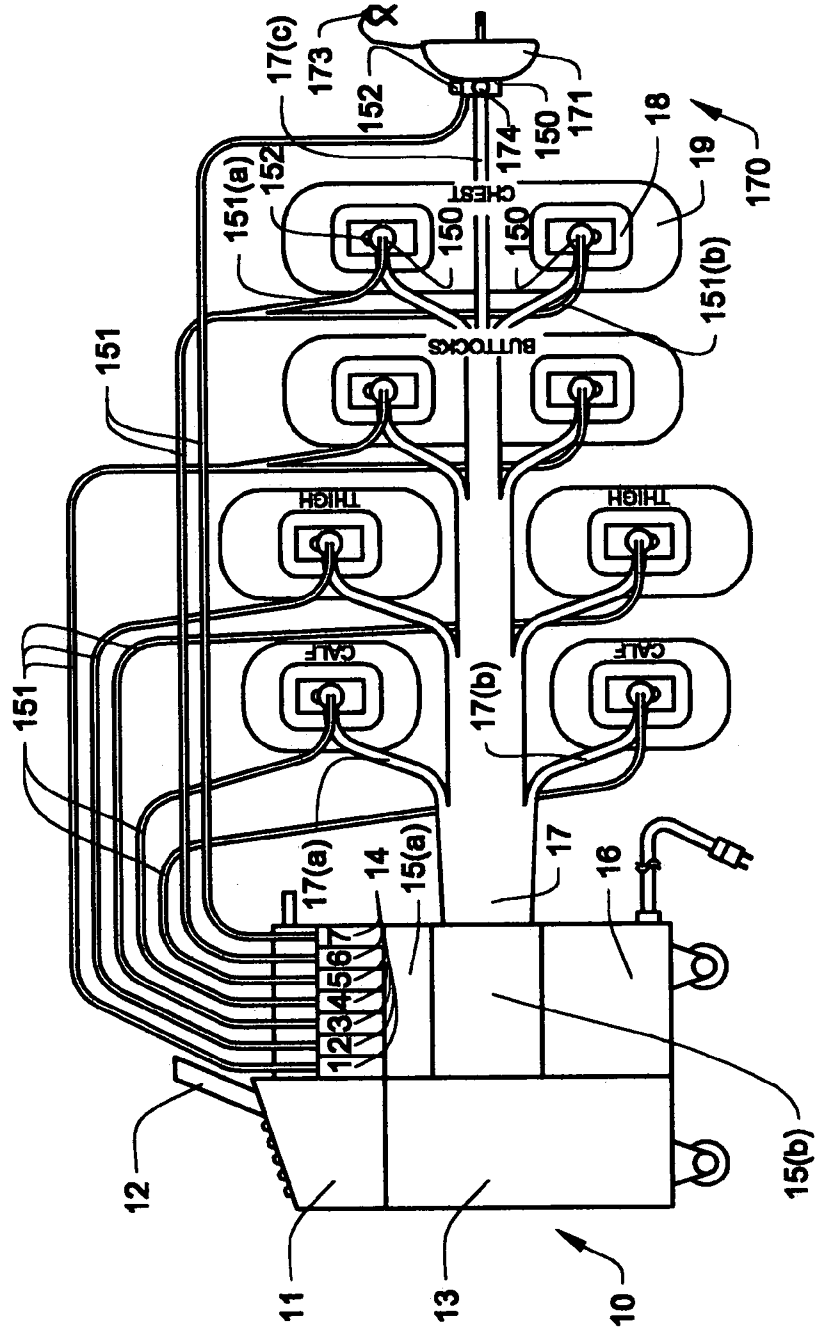

FIG. 13 illustrates a strongly preferred embodiment of the present invention, in which seven solenoid valves 14 are in fluid communication with high pressure air reservoir 15(*a*). One air pilot line 151 extends from the first solenoid valve 14 and branches into two branch pilot lines 151(*a*) and 151(*b*) as described above, each of which extends to one air controlled valve 150 mounted on and in fluid communication with each of the two bladders 18 disposed within buttocks cuff 19. One air pilot line 151 extends from each of the second through fifth solenoid valves 14 to one of the four air controlled valves 150 attached to one of the four bladders 18 of the calf and thigh cuffs 19. One air pilot line 151 extends from the sixth solenoid valve 14 and branches into two branch air pilot lines 151(*a*) and 151(*b*), each of which extends to one of the two air controlled valves 150 mounted on the two bladders 18 of chest cuff 19. One air pilot line 151 attached to the seventh solenoid valve 14 extends to a air controlled valve 150 mounted on mouthpiece assembly 170 (see FIG. 14), which includes soft rubber or plastic lip cover 171, air tube 172, nose pinch 173, and air pressure regulator 174, or on an intubation tube or mask; as described above. Four pairs of branch air hoses 17(*a*) and 17(*b*) and one branch air hose 17(*c*) extend from main air hose 17 in fluid communication with low pressure reservoir 15(*b*), each of which is removeably attached to one of the eight air controlled valves 150 mounted on the bladders 18 and the one air controlled valve mounted on mouthpiece assembly 170.

Alternatively, a mask over the patient's nose and mouth an intubation tube, as known in the art, may be used instead of the mouthpiece assembly described with respect to FIG. 13.

Figure 14:
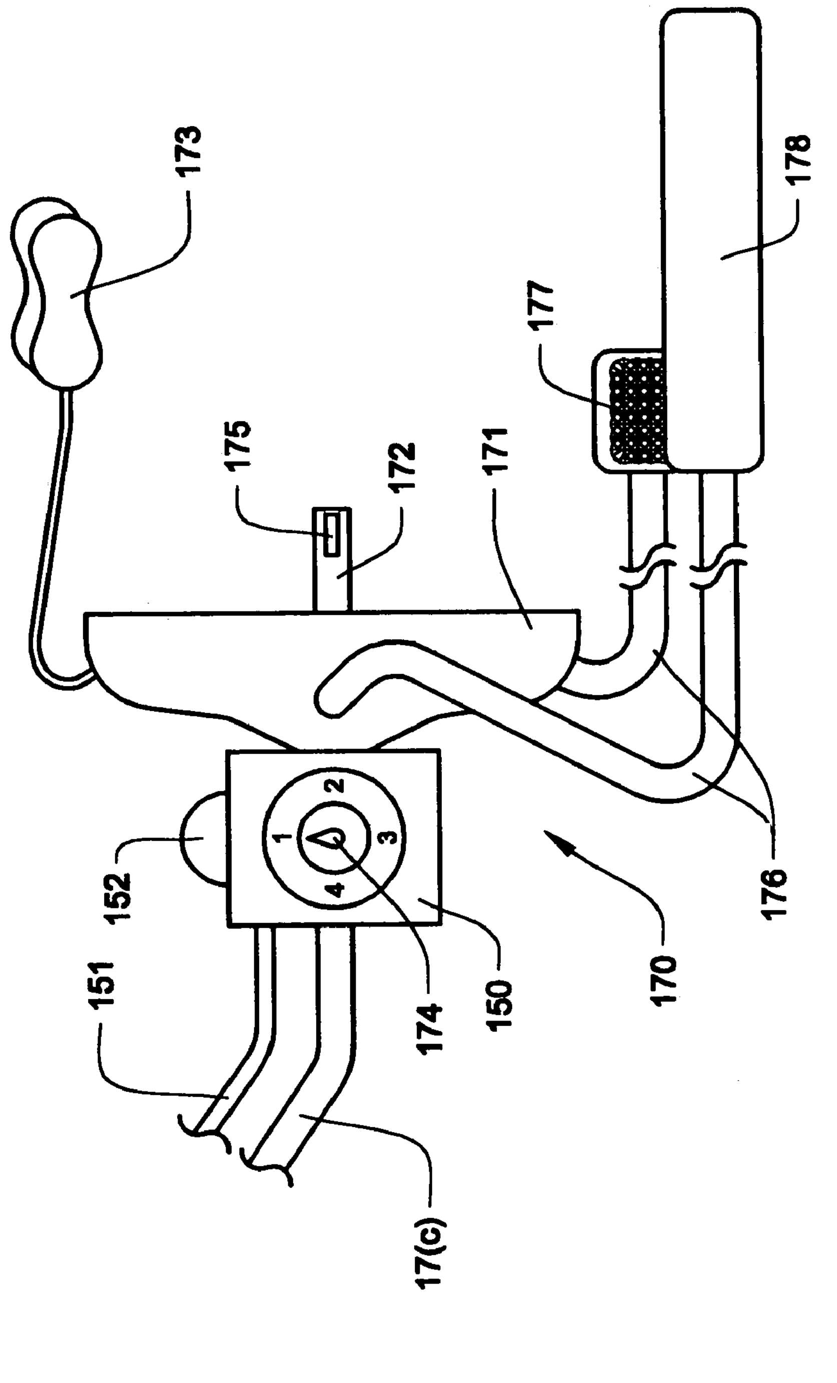
FIG. 14 is partial side view showing a mouthpiece and air pressure regulator thereof.

As shown in FIG. 14, the amount of air pressure to be released into the airway of a patient in cardiac arrest by actuation of air controlled valve 150 mounted on mouthpiece assembly 170, which is actuated by the seventh solenoid valve 14 through its associated air pilot line 151, may be manually set by the operator on air pressure regulator 174. The setting chosen for pressure regulator 174 is based on the patient's height and weight, so as not to overpressure the lungs. Alternatively, an air pressure sensor 175 mounted on air tube 172 can be interfaced by wire or telemetry, as known in the art, with microprocessor 11, which actuates, through air pilot line 151, the air actuated valve 150 mounted on mouthpiece assembly 170 and infuses the volume of air necessary to reach the pressure manually set by the operator or selected by pressing the breath pressure icon and up or down arrows on the drop-down Cardiac Arrest menu shown in FIG. 15. Optionally, microprocessor 11 can, based upon a wire or telemetry signal from air pressure sensor 175 mounted on air tube 172, allow air over the selected pressure to be released by an air relief or check valve (not separately shown) from exhaust port 152 into the atmosphere.

Head straps 176, terminating in short Velcro® pad 177 and wide Velcro pad 178, are attached about the patient's head and enable mouthpiece assembly 170 or a mask over the patient's mouth and nose to be held in place. Nose clip 173 is applied to the patient's nostrils to prevent air from escaping through his/her nose. In this embodiment, while four (4) settings, based on body size (small, medium, large and obese) of air pressure regulator 174 are shown, any individual selections, such as numbered by pressure or volume, can be used. It is understood that the air actuated valve 150 associated with the mouthpiece assembly 170 is a proportional valve controllable by the microprocessor 11, and may, alternatively, be attached to an intubation tube inserted into a patient's airway, to which an air pressure sensor or multi-function sensor may be attached, as aforesaid.

When treating a person suffering from CHF, air pressure sensor 175 can relay to microprocessor 11, by wire or telemetry, data on a variety of cardio-pulmonary and metabolic functions, such as VE/VC02, V02, ETC02 and respiration rate. Microprocessor 11, along with blood pressure, from the plethysmograph, and heart rate and trend from the ECG, can be programmed to adjust the compression pressure, and inception and duration of compression to maintain a desired peak diastolic/systolic augmentation ratio. Optionally, an air pressure sensor (not separately shown) can provide data to enable microprocessor 11 to limit the pressure or volume of air infused into the patient's lungs through mouthpiece 172 to a physiologically acceptable level, so as to not over-inflate the lungs.

Figure 15:
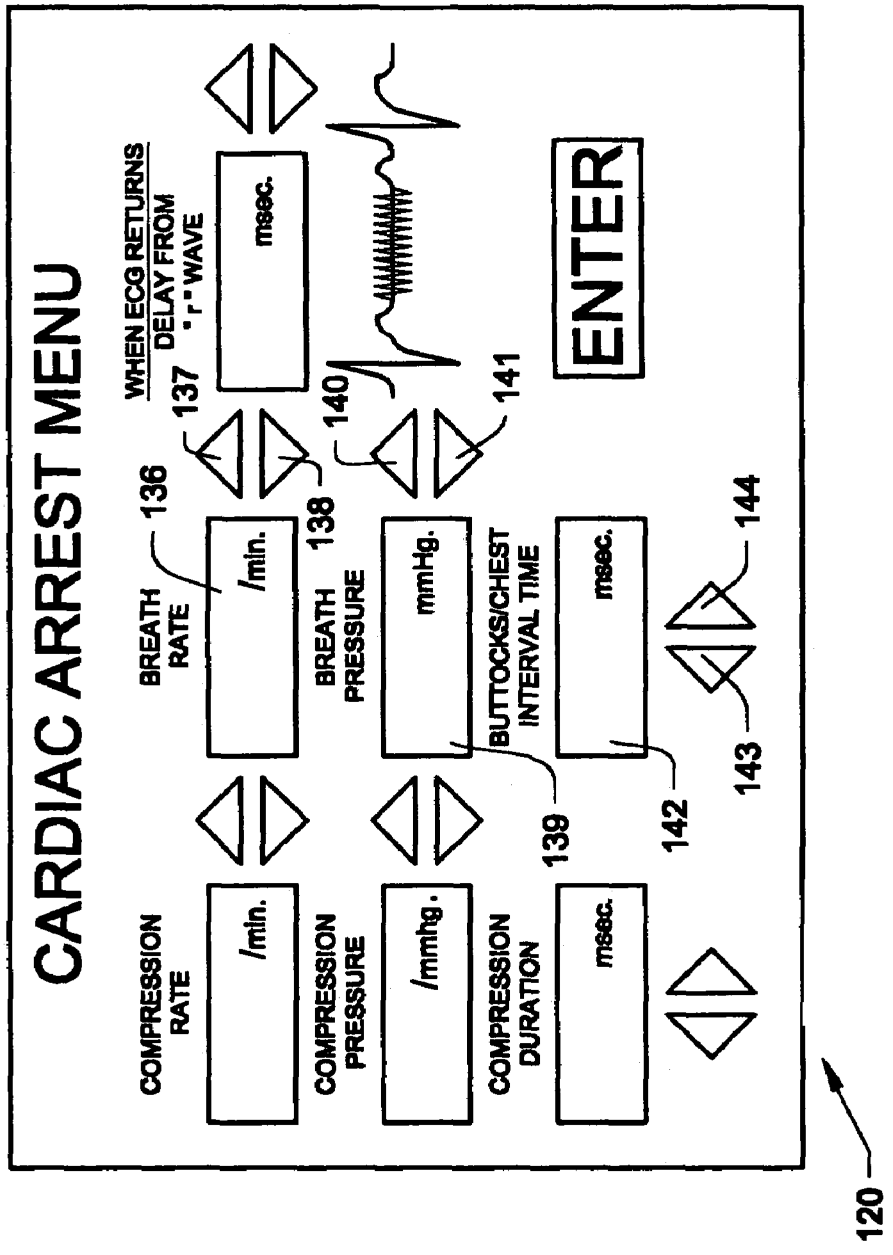

FIG. 15 shows drop-down Cardiac Arrest Menu 120, which appears when the "Arrest' icon 52 of display screen 20 of FIG. 3 is pressed, which also applies to the embodiment of FIG. 13. In addition to the displays and functions shown in FIG. 5, by pressing the "Breath Rate" icon 136 and up/down arrows 137 and 138, respectively, the number of actuations per minute of air controlled valve 150 of mouthpiece assembly 170 of the device of FIG. 13 can be selected by the operator and displayed, preferably about 12 to 16 per minute. By pressing the "Breath Pressure" icon 139 and up/down arrows 140 or 141, respectively, the pressure of the air allowed by air controlled valve 150 into mouthpiece assembly 170 of the device of FIG. 13 can be selected by the operator, based on the patient's height and weight, and displayed, as described above. For patient safety, a limit may be programmed into microprocessor 11 to prevent over-inflation of the lungs, or the air pressure regulator can be manually set, as described above relative to FIG. 14.

The interval between completion of compression of the buttocks cuff and the inception of compression of the chest cuff can be fixed, preferably at about 30 to 50 milliseconds. Alternatively, pressing the "Buttocks/Chest Interval Time" icon 142 and left or right arrows 143 or 144, respectively, the desired interval in milliseconds between the completion of compression of the buttocks cuff and the inception of compression of the chest cuff can be selected by the operator and displayed.

FIG. 16 illustrates the sequence of events which occurs when a function icon is selected on display screen 20 of a prior art ECP device, such as shown in FIG. 1. Selection of a function icon, such as Compression Pressure, Delay Time or Duration of Pressure, causes a signal to be sent to microprocessor 11, which actuates, at the pressure, delay time and duration chosen by the operator, the selected pair of air controlled valve 150 and allows pressurized air to inflate the selected pairs of bladders 18. This occurs in the following sequence: calves, thighs, and buttocks toward the heart, during diastole.

Figure 17:
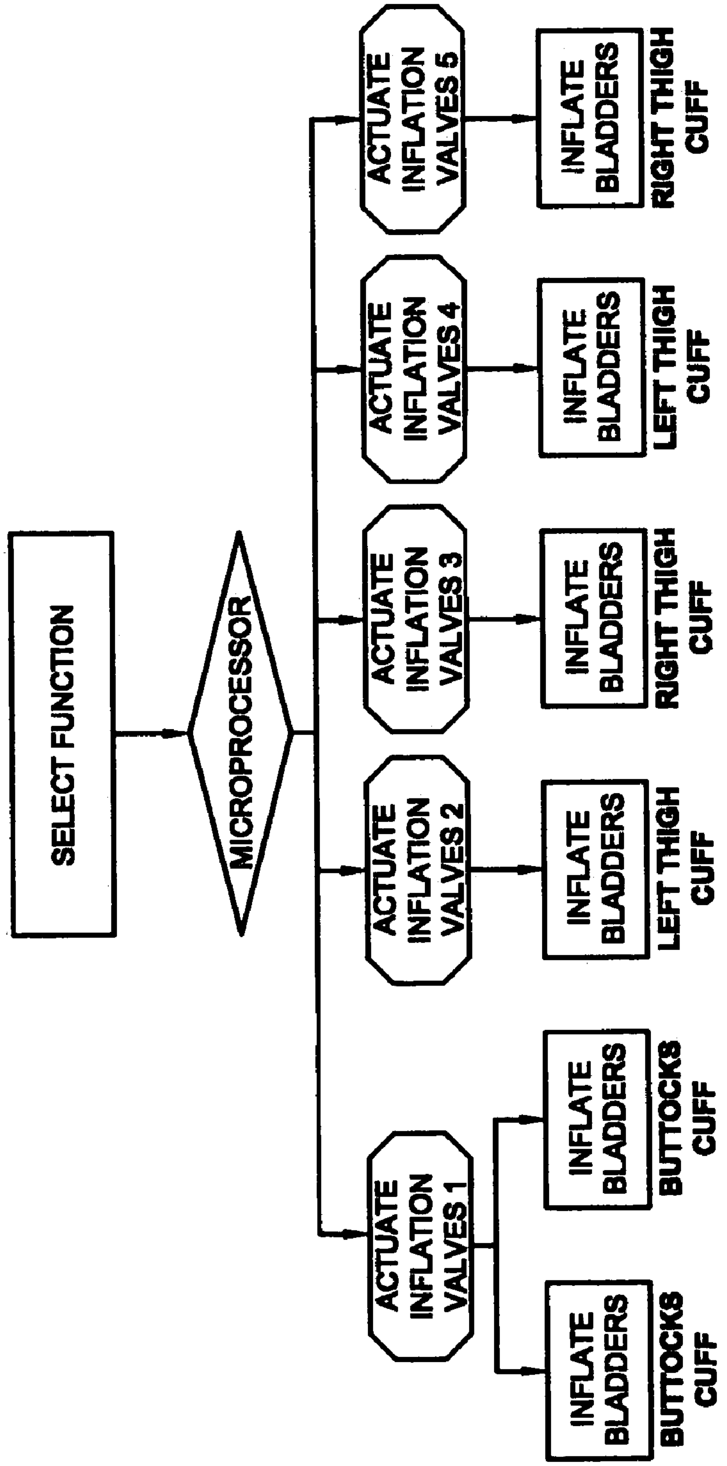
FIG. 17-19 are block diagrams of the preferred embodiments showing the elements of the present invention.

FIG. 17 illustrates the sequence of events that occur when a function icon of drop-down menus 60, 70 or 90 of the display screen 20 of the present invention device of FIG. 3 or drop-down menus 110 or 130 of the present invention device of FIG. 7 is pressed. Pressing a function icon sends a signal to microprocessor 11, which actuates or adjusts the inflation of bladders 18 related to air controlled valves 150 that are selected by the operator. This causes the selected bladders 18 to be inflated, in the order chosen, either during diastole or systole, at the selected delay time for the compression period and at the pressure selected by the operator. The significant additional control over what is offered by the prior art device is noted.

Figure 18:
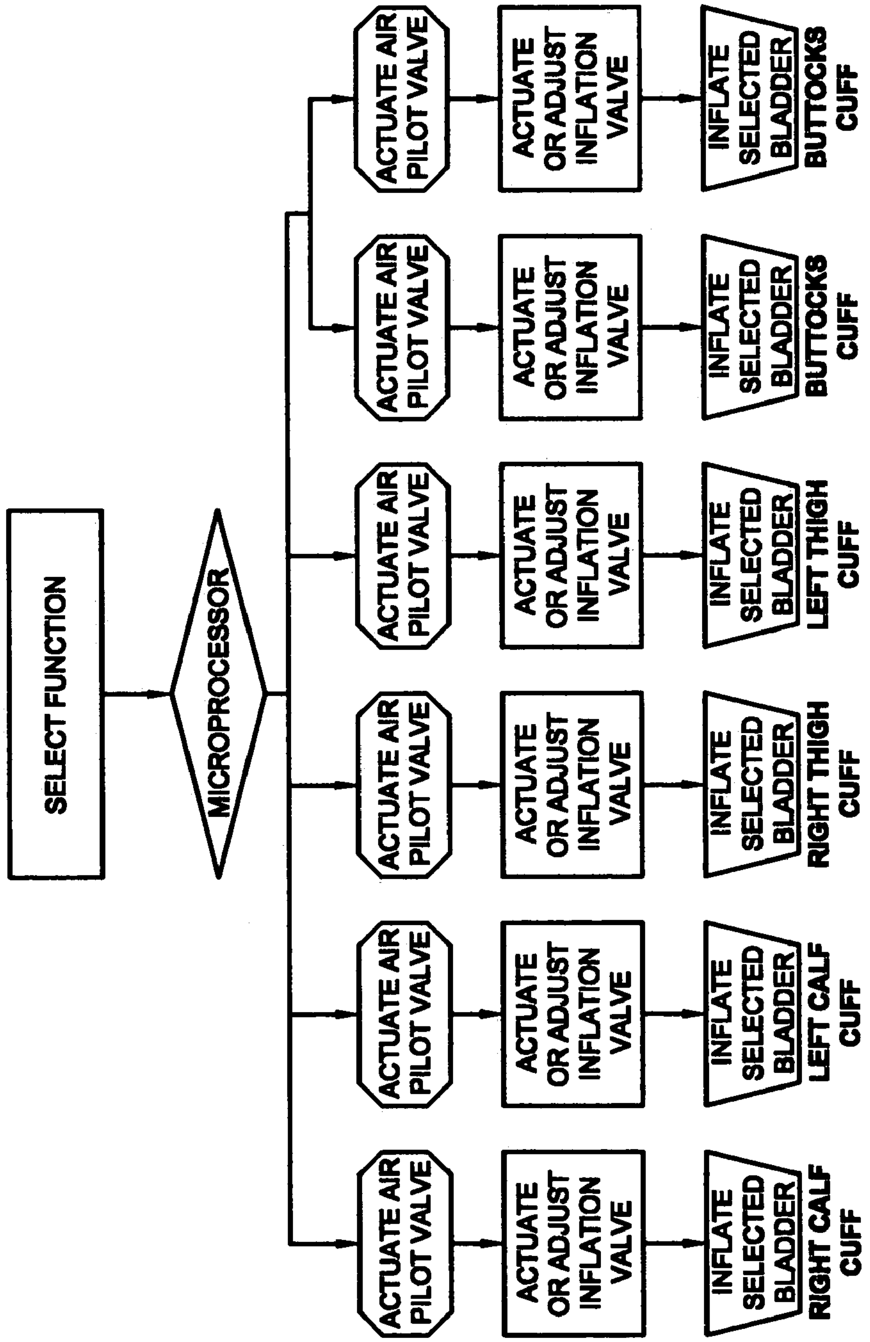

FIG. 18 illustrates the sequence of events which occurs when a function icon of display screen 20 of FIG. 3 or a function icon of the drop-down menus of FIGS. 4, 5, 6, 8 and 9 is pressed. Pressing a function icon causes a signal to be sent to microprocessor 11, which actuates the air controlled valves 150 that have been selected by the operator and adjusts the output of valves 150, inflating the corresponding bladders 18 selected by the operator, in such order and at such intervals, delay times, durations and pressures, during either diastole or systole, as chosen by the operator. The significant additional control over what is offered by the prior art device is noted.

Figure 19:
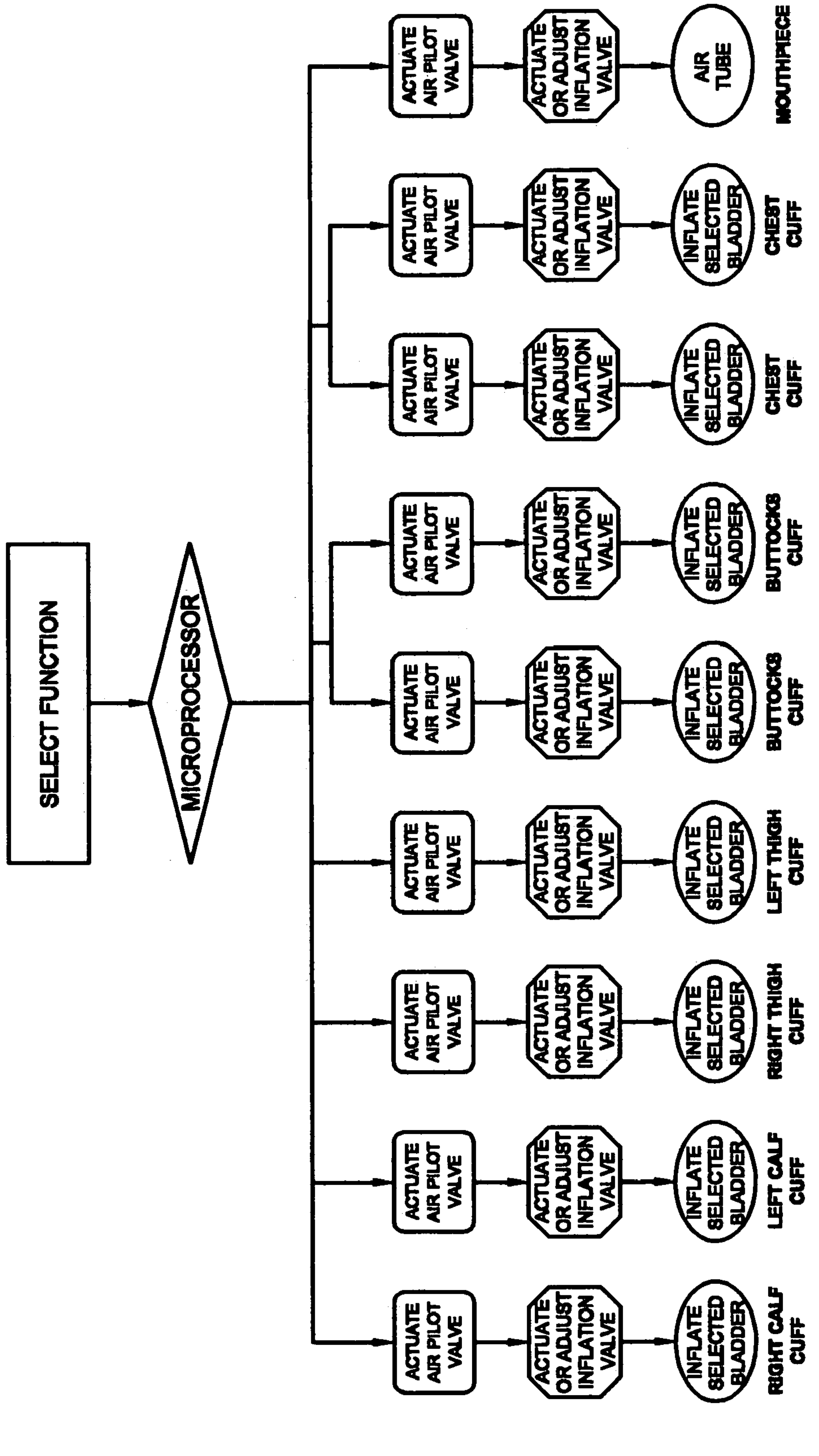

FIG. 19 illustrates the sequence of events that occur when a function icon of drop-down menu 120 (FIG. 15) of the preferred embodiment of the present invention shown in FIG. 13 is pressed. When a function icon is pressed, a signal is sent to microprocessor 11, which actuates the corresponding solenoid valves selected by the operator, actuating and adjusting the output of their associated air controlled valves 150 and inflating their associated bladders 18, and controlling the volume or pressure of air infused through air tube 172 of mouthpiece assembly 170 (FIG. 14), at such pressure, delay times and durations and in such order, during either diastole or systole, as may be selected by the operator. The significant additional control over what is offered by the prior art device is noted.

The words used in this specification to describe the invention and its various embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or elements of this described invention and its various embodiments are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the invention and its various embodiments below or that a single element may be substituted for two or more elements in a claim.

Changes from the claimed subject matter as viewed by a person with ordinary skill in the art, now known or later devised, are expressly contemplated as being equivalents within the scope of the invention and its various embodiments. Therefore, obvious substitutions now or later known to one with ordinary skill in the art are defined to be within the scope of the defined elements. The invention and its various embodiments are thus to be understood to include what is specifically illustrated and described above, what is conceptually equivalent, what can be obviously substituted, and also what essentially incorporates the essential idea of the invention.

While the invention has been described with reference to at least one preferred embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method of applying therapeutic pressure to exterior pressure points on a patient to treat a medical condition, the method comprising the steps of: sensing the patient's electrocardiogram and blood pressure and applying a selected magnitude of air pressure exteriorly to selected ones of the points on the patient during a selected time period during a cardiac cycle and controlling the peak diastolic pressure to peak systolic pressure ratio (D/S Ratio) in the treatment of persons with congestive heart failure and a left ventricular ejection fraction less than about 40% to not exceed the heart's capacity to eject a therapeutic portion of the blood in the heart's ventricles, wherein the D/S Ratio is held to not more than 0.7:1 to 0.8:1 during the first five hours of therapeutic pressure application.

2. The method of claim 1 further comprising the step of setting a residual pressure and maintaining said residual pressure in bladders engaged within cuffs on the pressure points of the patient.

3. The method of claim 2 further comprising the step of engaging a check valve on each of a plurality of air actuated valves to maintain a selected residual pressure in the bladders upon release of therapeutic pressure.

4. The method of claim 1 further comprising the step of selecting a sequence of therapeutic pressure applications to the pressure points on the patient from one of: toward the heart and toward the feet.

5. The method of claim 1 further comprising the step of selecting a therapeutic pressure application Initiation and completion during one of diastole and systole.

6. The method of claim 1 further comprising the step of selecting at least one point of therapeutic pressure application on a patient from the group of pressure points including the calves, thighs, buttocks, abdomen and chest.

7. The method of claim 1 further comprising the step of selecting a compression rate, compression therapeutic pressure and compression duration for each of the selected points of therapeutic pressure application in the absence of an ECG signal.

8. The method of claim 1 further comprising the step of adjusting intervals between therapeutic pressure applications on points.

9. The method of claim 1 further comprising the step of selecting and auto-maintaining a desired peek diastolic pressure to peak systolic pressure nitia by adjusting the magnitude of the therapeutic pressure application to the points on the patient.

10. The method of claim 9 further comprising the step of automatically adjusting the duration of a delay time from the "r" wave of a patient's ECG and the duration of therapeutic pressure application to maintain a selected D/S Ratio.

11. The method of claim 1 further comprising the step of selecting one of an acceptable minimum and maximum qrs width.

12. The method of claim 1 further comprising the step of placing air actuated valves at each of the points on the patent and separately providing therapeutic air pressure application to bladders associated with each of the points on the patent through the air actuated valves.

13. The method of claim 1 further comprising the step of applying the therapeutic pressure to the points on a patient, wherein the points are at least one of: the calves, thighs, buttocks, abdomen and chest.

14. The method of claim 1 further comprising the step of applying the therapeutic pressure, wherein at least one of the points is on the chest.

15. The method of claim 1 further comprising the step of applying the therapeutic pressure wherein at least one of the points is on the abdomen.

16. The method of claim 1 further comprising the steps of providing one of: a mouthpiece, a nose pinch assembly, an intubation tube and a mask, over at least one of the patient's nose and mouth; further providing thereon, an air actuated valve and an air pressure regulator, and applying air pressure into the patient's airway at a selected pressure, for a selected period of time and at a selected rate.

17. The method of claim 16 further comprising the step of setting an air pressure volume to be employed with one of the mouthpiece and nose pinch assembly, the intubation tube and the mask.

18. The method of claim 16 further comprising the step of applying an air pressure sensor feedback means for adjusting and maintaining a selected infusion volume.

19. The method of claim 16 further comprising the step of selecting one of a fixed plurality of pressure settings on the air pressure regulator.

20. The method of claim 16 further comprising the step of selecting a breath pressure, and breath rate.

21. The method of claim 1 further comprising the step of selecting a buttocks and a chest compression interval time for actuating the application of a therapeutic amount of pressure to each simultaneously for a selected duration.

22. The method of claim 1 further comprising the steps of selecting a function icon on the display screen; sending a signal to the microprocessor, actuating inflation of selected bladders at the desired points on the patient in a selected order with a selected delay time and compression period and at a selected pressure.

23. The method of claim 22 further comprising to step of actuating at least one air actuated valve and admitting a second relatively lower therapeutic pressure air through at least one air actuated valve to at least one air bladder for applying therapeutic pressure to at least one point on the patient.

24. The method of claim 1 further comprising the stop of alternately compressing at least one of the calves, thighs, buttocks and abdomen with the chest of a patient in cardiac arrest for selected time periods and therapeutic pressures in the absence or an ECG signal.

25. The method of claim 1 wherein to D/S Ratio is held to not more than 0.8:1 to 0.9:1 during a five to ten hour duration of therapeutic pressure application.

26. The method of claim 1 wherein to D/S Ratio is held to not more than 0.9:1 to 1.3:1 during a 35 hour therapeutic pressure application.

27. The method of claim 1 wherein the therapeutic pressure application is held to not more frequent than one hour per day.

28. The method of claim 1 wherein the therapeutic pressure application is bold to not more frcquent than one hour every other day.

29. The method of claim 1 wherein in treating septic shock, at least two of the calves, thighs, buttocks and abdomen of a patient are therapeutically compressed during systole in a sequence moving toward the heart.

30. The method of claim 1 wherein in treating peripheral edema, at least two of the calves, thighs, buttocks and abdomen of a patient are sequentially compressed during one of systole and diastole in a sequence moving in the direction of one of toward the heart and toward the feet.

31. The method of claim 1 wherein in treating a patient in whom a femoral catheter is deployed, a therapeutic pressure is applied only to the calves and thighs of said patient.

32. The method of claim 25 further comprising the step of, for a person with congestive heart thilure, reducing the patient's target D/S ratio in proportion to the degree the patient's left ventricular ejection fraction is below about 40%.

* * * * *

UNITED STATES PATENT AND TRADEMARK OFFICE
CERTIFICATE OF CORRECTION

PATENT NO. : 7,244,225 B2
APPLICATION NO. : 10/681812
DATED : July 17, 2007
INVENTOR(S) : Loeb et al.

It is certified that error appears in the above-identified patent and that said Letters Patent is hereby corrected as shown below:

Column 25, line 4, change “40%” to --40%, --; line 22, change “Initiation” to --initiation--; line 37, change “peek” to --peak--; line 38, change “nitia” to --ratio--;

Column 26, lines 25, 36, and 39, change “to” to --the--; line 31, change “stop” to --step--; line 46, change “bold” to --held--, and “frcquent” to --frequent--; line 60, change “claim 25” to --claim 1--; and line 61, change “thilure” to --failure--.

Signed and Sealed this

Eighteenth Day of December, 2007

JON W. DUDAS
*Director of the United States Patent and Trademark Office*